US009198861B2

(12) United States Patent
Park et al.

(10) Patent No.: US 9,198,861 B2
(45) Date of Patent: *Dec. 1, 2015

(54) METHODS OF PRODUCING STABILIZED SOLID DOSAGE PHARMACEUTICAL COMPOSITIONS CONTAINING MORPHINANS

(75) Inventors: Jae Han Park, Olivette, MO (US); Tiffani Eisenhauer, Columbia, IL (US); Anish Dhanarajan, Kirkwood, MO (US); Vishal K. Gupta, Ballwin, MO (US); Stephen Overholt, St. Louis, MO (US)

(73) Assignee: MALLINCKRODT LLC, Hazelwood, MO (US)

( * ) Notice: Subject to any disclaimer, the term of this patent is extended or adjusted under 35 U.S.C. 154(b) by 8 days.

This patent is subject to a terminal disclaimer.

(21) Appl. No.: 13/995,810

(22) PCT Filed: Jun. 22, 2011

(86) PCT No.: PCT/US2011/041533
§ 371 (c)(1),
(2), (4) Date: Jun. 19, 2013

(87) PCT Pub. No.: WO2012/087377
PCT Pub. Date: Jun. 28, 2012

(65) Prior Publication Data
US 2013/0273153 A1 Oct. 17, 2013

Related U.S. Application Data

(63) Continuation-in-part of application No. 12/973,962, filed on Dec. 21, 2010.

(60) Provisional application No. 61/284,651, filed on Dec. 22, 2009.

(30) Foreign Application Priority Data

Dec. 21, 2010 (WO) ................ PCT/US2010/061400

(51) Int. Cl.
A61K 9/16 (2006.01)
A61K 9/20 (2006.01)
A61K 31/167 (2006.01)
A61K 31/485 (2006.01)
A61K 45/06 (2006.01)
A61K 31/439 (2006.01)
A61K 9/24 (2006.01)

(52) U.S. Cl.
CPC . *A61K 9/16* (2013.01); *A61K 9/209* (2013.01); *A61K 9/2031* (2013.01); *A61K 9/2095* (2013.01); *A61K 31/167* (2013.01); *A61K 31/439* (2013.01); *A61K 31/485* (2013.01); *A61K 45/06* (2013.01); *A61K 9/2077* (2013.01)

(58) Field of Classification Search
None
See application file for complete search history.

(56) References Cited

U.S. PATENT DOCUMENTS

| | | |
|---|---|---|
| 4,713,243 A | 12/1987 | Schiraldi et al. |
| 4,851,226 A | 7/1989 | Julian et al. |
| 4,894,236 A | 1/1990 | Jang |
| 4,996,058 A | 2/1991 | Sinnreich |
| 5,075,114 A | 12/1991 | Roche |
| 5,266,331 A | 11/1993 | Oshlack et al. |
| 5,336,691 A | 8/1994 | Raffa et al. |
| 5,478,577 A | 12/1995 | Sackler et al. |
| 5,508,042 A | 4/1996 | Oshlack et al. |
| 5,549,912 A | 8/1996 | Oshlack et al. |
| 5,582,837 A | 12/1996 | Shell |
| 5,626,874 A | 5/1997 | Conte et al. |
| 5,656,295 A | 8/1997 | Oshlack et al. |
| 5,672,360 A | 9/1997 | Sackler et al. |
| 5,783,212 A | 7/1998 | Fassihi et al. |
| 5,866,161 A | 2/1999 | Childers et al. |
| 5,876,759 A | 3/1999 | Gowan, Jr. |
| 5,891,471 A | 4/1999 | Miller et al. |
| 5,945,123 A | 8/1999 | Hermelin |
| 5,945,125 A | 8/1999 | Kim |
| 5,958,459 A | 9/1999 | Chasin et al. |
| 5,965,161 A | 10/1999 | Oshlack et al. |
| 5,965,163 A | 10/1999 | Miller et al. |
| 5,965,167 A | 10/1999 | Sanghvi et al. |
| 5,968,551 A | 10/1999 | Oshlack et al. |
| 5,972,389 A | 10/1999 | Shell et al. |
| 5,980,882 A | 11/1999 | Eichman |
| 6,024,982 A | 2/2000 | Oshlack et al. |

(Continued)

FOREIGN PATENT DOCUMENTS

| | | |
|---|---|---|
| EP | 159852 | 10/1985 |
| EP | 1140026 | 6/2000 |

(Continued)

OTHER PUBLICATIONS

Requirement for Restriction/Election received in U.S. Appl. No. 13/166,770 and dated Jun. 22, 2012 (6 pages).
Non-Final Office Action received in U.S. Appl. No. 13/166,770 and dated Nov. 26, 2012 (14 pages).
Non-Final Office Action received in U.S. Appl. No. 14/092,375 and dated Feb. 24, 2014 (11 pages).
Requirement for Restriction/Election received in U.S. Appl. No. 13/473,563 and dated Sep. 11, 2012 (5 pages).
Non-Final Office Action received in U.S. Appl. No. 13/473,563 and dated May 6, 2013 (20 pages).
Non-Final Office Action received in U.S. Appl. No. 14/109,052 and dated Apr. 25, 2014 (6 pages).
Final Office Action received in U.S. Appl. No. 14/109,052 and dated Aug. 11, 2014 (7 pages).
Requirement for Restriction/Election received in U.S. Appl. No. 13/473,586 and dated Mar. 28, 2013 (6 pages).

(Continued)

*Primary Examiner* — Frederick Krass
*Assistant Examiner* — Michael P Cohen
(74) *Attorney, Agent, or Firm* — Mayer Brown LLP

(57) ABSTRACT

Methods for producing stabilized solid dosage form pharmaceutical compositions are provided. In particular, methods for preparing protected granules containing morphinans, and solid dosage form pharmaceutical compositions produced using the morphinan-protected granules are provided.

10 Claims, No Drawings

(56) References Cited

U.S. PATENT DOCUMENTS

| | | | |
|---|---|---|---|
| 6,068,855 A | 5/2000 | Leslie et al. | |
| 6,071,208 A | 6/2000 | Koivunen | |
| 6,103,219 A | 8/2000 | Sherwood et al. | |
| 6,103,261 A | 8/2000 | Chasin et al. | |
| 6,126,969 A | 10/2000 | Shah et al. | |
| 6,143,322 A | 11/2000 | Sackler et al. | |
| 6,210,714 B1 | 4/2001 | Oshlack et al. | |
| 6,245,357 B1 | 6/2001 | Edgren et al. | |
| 6,254,887 B1 | 7/2001 | Miller et al. | |
| 6,340,475 B2 | 1/2002 | Shell et al. | |
| 6,372,254 B1 | 4/2002 | Ting et al. | |
| 6,375,957 B1 | 4/2002 | Kaiko et al. | |
| 6,387,404 B2 | 5/2002 | Oshlack et al. | |
| 6,488,962 B1 | 12/2002 | Berner et al. | |
| 6,488,963 B1 | 12/2002 | McGinity et al. | |
| 6,500,459 B1 | 12/2002 | Chhabra et al. | |
| 6,599,529 B1 | 7/2003 | Skinhoj et al. | |
| 6,635,280 B2 | 10/2003 | Shell et al. | |
| 6,667,060 B1 | 12/2003 | Vandecruys et al. | |
| 6,682,759 B2 | 1/2004 | Lim et al. | |
| 6,696,066 B2 | 2/2004 | Kaiko et al. | |
| 6,706,281 B2 | 3/2004 | Oshlack et al. | |
| 6,723,340 B2 | 4/2004 | Gusler et al. | |
| 6,730,321 B2 | 5/2004 | Ting et al. | |
| 6,733,783 B2 | 5/2004 | Oshlack et al. | |
| 6,797,283 B1 | 9/2004 | Edgren et al. | |
| 6,852,336 B2 | 2/2005 | Hunter et al. | |
| 6,902,742 B2 | 6/2005 | Devane et al. | |
| 7,074,430 B2 | 7/2006 | Miller et al. | |
| 7,201,920 B2 | 4/2007 | Kumar et al. | |
| 7,374,781 B2 | 5/2008 | Zhang et al. | |
| 7,405,238 B2 | 7/2008 | Markey et al. | |
| 7,413,751 B2 | 8/2008 | Devane et al. | |
| 7,438,927 B2 | 10/2008 | Berner et al. | |
| 7,514,100 B2 | 4/2009 | Oshlack et al. | |
| 7,674,799 B2 | 3/2010 | Chapman et al. | |
| 7,683,072 B2 | 3/2010 | Chapman et al. | |
| 7,691,873 B2 | 4/2010 | Duncalf et al. | |
| 7,776,314 B2 | 8/2010 | Bartholomaus et al. | |
| 7,846,476 B2 | 12/2010 | Oshlack et al. | |
| 7,897,172 B2 | 3/2011 | Qasem et al. | |
| 7,939,543 B2 | 5/2011 | Kupper | |
| 7,943,170 B2 | 5/2011 | Chan et al. | |
| 7,976,870 B2 | 7/2011 | Berner et al. | |
| 8,075,872 B2 | 12/2011 | Arkenau-Maric et al. | |
| 2001/0008639 A1 | 7/2001 | Oshlack et al. | |
| 2002/0018810 A1 | 2/2002 | Oshlack et al. | |
| 2002/0058050 A1 | 5/2002 | Sackler et al. | |
| 2002/0192277 A1 | 12/2002 | Oshlack et al. | |
| 2003/0035837 A1 | 2/2003 | Sackler et al. | |
| 2003/0044466 A1 | 3/2003 | Markey et al. | |
| 2003/0091635 A1 | 5/2003 | Baichwal et al. | |
| 2003/0092724 A1 | 5/2003 | Kao et al. | |
| 2003/0099704 A1 | 5/2003 | Oshlack et al. | |
| 2003/0104062 A1 | 6/2003 | Berner et al. | |
| 2004/0096500 A1 | 5/2004 | Oshlack et al. | |
| 2004/0105887 A1 | 6/2004 | Oshlack et al. | |
| 2004/0131671 A1 | 7/2004 | Zhang et al. | |
| 2004/0156899 A1 | 8/2004 | Louie-Helm et al. | |
| 2005/0013863 A1 | 1/2005 | Lim et al. | |
| 2005/0020613 A1 | 1/2005 | Boehm et al. | |
| 2005/0031546 A1 | 2/2005 | Bartholomaus et al. | |
| 2005/0089570 A1 | 4/2005 | Cruz et al. | |
| 2005/0106249 A1 | 5/2005 | Hwang et al. | |
| 2005/0112195 A1 | 5/2005 | Cruz et al. | |
| 2005/0158382 A1 | 7/2005 | Cruz et al. | |
| 2005/0165038 A1 | 7/2005 | Gordon | |
| 2005/0232987 A1 | 10/2005 | Srinivasan et al. | |
| 2005/0266032 A1 | 12/2005 | Srinivasan et al. | |
| 2005/0267189 A1 | 12/2005 | Gao et al. | |
| 2006/0002860 A1 | 1/2006 | Bartholomaus et al. | |
| 2006/0057210 A1 | 3/2006 | Oshlack et al. | |
| 2006/0099255 A1 | 5/2006 | Oshlack et al. | |
| 2006/0165791 A1 | 7/2006 | Oshlack et al. | |
| 2006/0193782 A1 | 8/2006 | Bartholomaus et al. | |
| 2006/0205752 A1 | 9/2006 | Whitehead | |
| 2006/0240105 A1 | 10/2006 | Devane et al. | |
| 2006/0251721 A1 | 11/2006 | Cruz et al. | |
| 2006/0263436 A1 | 11/2006 | Baert et al. | |
| 2006/0269604 A1 | 11/2006 | Sackler et al. | |
| 2006/0292214 A1 | 12/2006 | Jenkins et al. | |
| 2007/0020335 A1 | 1/2007 | Chen et al. | |
| 2007/0048228 A1 | 3/2007 | Arkenau-Maric et al. | |
| 2007/0059359 A1 | 3/2007 | Backensfeld et al. | |
| 2007/0128279 A1 | 6/2007 | Edgren et al. | |
| 2007/0183980 A1 | 8/2007 | Arkenau-Maric et al. | |
| 2007/0184112 A1 | 8/2007 | Wong et al. | |
| 2007/0190142 A1 | 8/2007 | Breitenbach et al. | |
| 2007/0207200 A1* | 9/2007 | Plachetka et al. | 424/472 |
| 2007/0237833 A1 | 10/2007 | Sackler et al. | |
| 2007/0259033 A1 | 11/2007 | Cruz | |
| 2007/0259045 A1 | 11/2007 | Mannion et al. | |
| 2007/0275065 A1 | 11/2007 | Oshlack et al. | |
| 2007/0281018 A1 | 12/2007 | Qiu et al. | |
| 2008/0020039 A1 | 1/2008 | Parikh et al. | |
| 2008/0031901 A1 | 2/2008 | Qiu et al. | |
| 2008/0031963 A1 | 2/2008 | Sackler et al. | |
| 2008/0044482 A1 | 2/2008 | Oshlack et al. | |
| 2008/0057122 A1 | 3/2008 | Toney-Parker et al. | |
| 2008/0113025 A1 | 5/2008 | Devane et al. | |
| 2008/0132532 A1 | 6/2008 | Wright et al. | |
| 2008/0138422 A1 | 6/2008 | Staniforth | |
| 2008/0220062 A1 | 9/2008 | Ashton | |
| 2009/0022798 A1 | 1/2009 | Rosenberg et al. | |
| 2009/0028941 A1 | 1/2009 | Cowles et al. | |
| 2009/0068269 A1 | 3/2009 | Oshlack et al. | |
| 2009/0081290 A1 | 3/2009 | McKenna et al. | |
| 2009/0149479 A1 | 6/2009 | Jenkins et al. | |
| 2009/0155357 A1 | 6/2009 | Muhuri | |
| 2009/0175937 A1 | 7/2009 | Rahmouni et al. | |
| 2009/0202629 A1 | 8/2009 | Oshlack et al. | |
| 2009/0304793 A1 | 12/2009 | Boehm | |
| 2009/0306119 A1 | 12/2009 | Keane | |
| 2009/0311320 A1 | 12/2009 | Oury et al. | |
| 2009/0317355 A1 | 12/2009 | Roth et al. | |
| 2009/0324714 A1 | 12/2009 | Liu et al. | |
| 2010/0010030 A1 | 1/2010 | Jain et al. | |
| 2010/0015222 A1 | 1/2010 | Han et al. | |
| 2010/0034876 A1 | 2/2010 | Oshlack et al. | |
| 2010/0040681 A1 | 2/2010 | Park et al. | |
| 2010/0092570 A1 | 4/2010 | Oshlack et al. | |
| 2010/0168148 A1 | 7/2010 | Wright et al. | |
| 2010/0172974 A1 | 7/2010 | Oshlack et al. | |
| 2010/0172989 A1 | 7/2010 | Roth et al. | |
| 2010/0196425 A1 | 8/2010 | Cruz et al. | |
| 2010/0196471 A1 | 8/2010 | Jain et al. | |
| 2010/0196474 A1 | 8/2010 | Han et al. | |
| 2010/0216829 A2 | 8/2010 | Kumar et al. | |
| 2010/0221293 A1 | 9/2010 | Cruz et al. | |
| 2010/0239662 A1 | 9/2010 | Rahmouni et al. | |
| 2010/0260833 A1 | 10/2010 | Bartholomaus et al. | |
| 2011/0020451 A1 | 1/2011 | Bartholomaus et al. | |
| 2011/0038927 A1 | 2/2011 | Oshlack et al. | |
| 2011/0038930 A1 | 2/2011 | Barnscheid et al. | |
| 2011/0052685 A1 | 3/2011 | Hou et al. | |
| 2011/0077238 A1 | 3/2011 | Leech et al. | |
| 2011/0117196 A1 | 5/2011 | Gordon | |
| 2011/0118189 A1 | 5/2011 | Farr et al. | |
| 2011/0129507 A1 | 6/2011 | Cruz | |
| 2011/0150969 A1 | 6/2011 | Shah et al. | |
| 2011/0150970 A1 | 6/2011 | Shah et al. | |
| 2011/0150971 A1 | 6/2011 | Shah et al. | |
| 2011/0150990 A1 | 6/2011 | Shah et al. | |
| 2011/0150991 A1 | 6/2011 | Shah et al. | |
| 2011/0159046 A1 | 6/2011 | Cruz | |
| 2011/0166171 A1 | 7/2011 | Qiu et al. | |
| 2011/0177168 A1 | 7/2011 | Chan et al. | |
| 2011/0195116 A1 | 8/2011 | Hobbs et al. | |
| 2011/0195989 A1 | 8/2011 | Rudnic et al. | |
| 2011/0207762 A1 | 8/2011 | Chapman et al. | |
| 2011/0212173 A1 | 9/2011 | Young et al. | |
| 2011/0229526 A1 | 9/2011 | Rosenberg et al. | |
| 2011/0229533 A1 | 9/2011 | Edgren et al. | |
| 2011/0262532 A1 | 10/2011 | Oshlack et al. | |

(56) References Cited

U.S. PATENT DOCUMENTS

| | | | |
|---|---|---|---|
| 2011/0301129 | A1 | 12/2011 | Berner et al. |
| 2011/0318392 | A1 | 12/2011 | Cruz et al. |
| 2012/0321713 | A1 | 12/2012 | Han et al. |

FOREIGN PATENT DOCUMENTS

| | | | |
|---|---|---|---|
| WO | 9718814 | | 5/1997 |
| WO | 9855107 | | 12/1998 |
| WO | 02/36099 | A1 | 5/2002 |
| WO | 03024426 | | 3/2003 |
| WO | 2005013863 | | 2/2005 |
| WO | 2005030182 | | 4/2005 |
| WO | 2006022759 | | 3/2006 |
| WO | 2006071208 | | 7/2006 |
| WO | 2007/103113 | A2 | 9/2007 |
| WO | 2008/015220 | A1 | 2/2008 |
| WO | 2008015221 | | 2/2008 |
| WO | 2009049405 | | 4/2009 |
| WO | 2009076764 | | 6/2009 |
| WO | 2009114648 | | 9/2009 |
| WO | 2009135846 | | 11/2009 |
| WO | 2010032128 | | 3/2010 |
| WO | 2010069050 | | 6/2010 |
| WO | 2010078486 | | 7/2010 |
| WO | 2010141505 | | 12/2010 |
| WO | 2011009603 | | 1/2011 |
| WO | 2011009604 | | 1/2011 |
| WO | 2011068723 | | 6/2011 |
| WO | 2011077451 | | 6/2011 |
| WO | 2011106416 | | 9/2011 |
| WO | 2012007159 | | 1/2012 |
| WO | 2012/087377 | A1 | 6/2012 |

OTHER PUBLICATIONS

Non-Final Office Action received in U.S. Appl. No. 13/473,586 and dated Aug. 2, 2013 (9 pages).
Non-Final Office Action received in U.S. Appl. No. 13/473,586 and dated Jun. 19, 2014 (7 pages).
Non-Final Office Action received in U.S. Appl. No. 13/473,571 and dated Aug. 31, 2012 (11 pages).
Final Office Action received in U.S. Appl. No. 13/473,571 and dated May 15, 2013 (16 pages).
Requirement for Restriction/Election received in U.S. Appl. No. 13/473,584 and dated Jun. 18, 2013 (15 pages).
Non-Final Office Action received in U.S. Appl. No. 13/473,584 and dated Oct. 24, 2013 (14 pages).
Final Office Action received in U.S. Appl. No. 13/473,584 and dated Aug. 20, 2014 (14 pages).
Non-Final Office Action received in U.S. Appl. No. 13/473,578 and dated Mar. 26, 2013 (11 pages).
Final Office Action received in U.S. Appl. No. 13/473,578 and dated Dec. 17, 2013 (7 pages).
Non-Final Office Action received in U.S. Appl. No. 14/479,129 and dated Apr. 14, 2015 (10 pages).
Requirement for Restriction/Election received in U.S. Appl. No. 14/187,939 and dated Jan. 23, 2015 (7 pages).
Requirement for Restriction/Election received in U.S. Appl. No. 14/188,582 and dated Jan. 29, 2015 (7 pages).
Non-Final Office Action received in U.S. Appl. No. 12/973,962 and dated Feb. 24, 2012 (13 pages).
Final Office Action received in U.S. Appl. No. 12/973,962 and dated Sep. 21, 2012 (15 pages).
Advisory Action received in U.S. Appl. No. 12/973,962 and dated Dec. 5, 2012 (3 pages).
Non-Final Office Action received in U.S. Appl. No. 12/973,962 and dated Jun. 19, 2014 (17 pages).
Final Office Action received in U.S. Appl. No. 12/973,962 and dated Apr. 20, 2015 (20 pages).
International Preliminary Report on Patentability for PCT/US2011/041533 dated Jun. 25, 2013 (7 pages).
International Search Report for PCT/US2011/041533 dated Apr. 24, 2012 (4 pages).
International Preliminary Report on Patentability for PCT/US2010/061400 dated May 16, 2012 and the Response to the written opinion in PCT/US2010/061400 (18 pages).
Written Opinion for PCT/US2010/061400 (5 pages).
Banfai B. Ganzler K, Kemeny S. Content uniformity and assay requirements in current regulations. J Chromatogr A. Jul. 13, 2007;1156(1-2):206-12. Epub Nov. 15, 2006.
Zhu Y, Shah NH Malick AW, Infeld MH, McGinity JW. Solid-state plasticization of an acrylic polymer with chlorpheniramine maleate and triethyl citrate. Int J Pharm. Jul. 25, 2002; 241(2):301-10.
Nimmo, W.S. et al., "Inhibition of Gastric Empyting and Drug Absorption by Narcotic Analgesics", Br. J. Clin. Pharmac., 2:509-513 (1975).
Altaf S A et al., "Bead Compacts II. Evaluation of Rapidly Disintegrating Nonsegregating Compressed Bead Formulations"; Drug Development and Industrial Pharmacy, New York, NY, US, vol. 25, No. 5, May 1, 1999; pp. 635-642.
International Search Report from Application No. PCT/US2010/061400 with a mailing date of Nov. 25, 2011.
Endo Pharmaceuticals Package Insert for Percocet(Oxycodone and Acetaminophen Tablets, USP); pp. 1-17.
www.fda.gov/Drugs/DrugSafety/ucm239821.htm; U.S. Department of Health & Human Services; FDA Drugs Safety Communication: Prescription Acetaminophen Products to be Limited to 325mg per Dosage Unit; Boxed Warning Will Highlight Potential for Severe Liver Failure; pp. 1-5.
Tylenol Professional Product Information(2010); McNeil Consumer Healthcare; pp. 1-59.
Oxycontin Description and Patient Information; pp. 1-32.
Cooperman et al; "A Novel Extended-Release Formulation of Oxycodone/Acetaminophen with Abuse Deterrent Properties"; Abstract; 2pgs.
Freed et al., "pH control of nucleophilic/electrophilic oxidation", Int., J. Of Pharm. 357, 2008, pp. 180-188.
Waterman et al., "Stabilization of Pharmaceuticals to Oxidative Degradation", Pharm. Dev. Tech., 7(1), 2002, pp. 1-32.
Degradation of Water-Soluble Resins, Technical Data, Polyox Water-Soluble Resins, Form 326-00027-1002AMS, 2002.
"Water-Soluble Resin Storage Stability", Technical Data, polyox Water-Soluble Resins, Form No. 326-00044-0704MAB, 2004.
Aulton M.E. "Aulton's Pharmaceutics: The Design and Manufacture of Medicines," Elsevier Limited, Oxford, Third Edition, 2007, pp. 270-278.
Prinderre et al., "Advances in Gastro Retentive Drug-Delivery Systems," Expert Opin. Drug Deliv. 8(9), pp. 1189-1203 (Sep. 2011).
Berner et al., "Case Studies in Swelling Polymeric Gastric Retentive Tablets," Expert Opin. Drug. Deliv., 3(4), p. 541-548 (Jul. 2006).
Gralise Prescribing Information, 24 pages.
Glumetza Prescribing Information, 10 pages.
Tylenol®Professional Product Information, 62 pages.
Foremost NF Flo Lactose, A spray-dried mixture of crystalline and amorphose lactose:, Foremost Farms USA, 1pg., Online Article downloaded from the site: http://www.foremostfarms.com/Comemrcial/pdfs/Specification/TDS NF Lactose 31 6.pdf, Document created on Jan. 28, 2010.
International Search Report from related PCT Patent application No.: PCT/US2009/036864 mailed Aug. 31, 2009, application now published as PCT Publication No.: WO2009/1146648 on Sep. 17, 2009.
Lab Basics Technical Library, Particle Size Conversion Table, Sigma-Aldrich, 3 pgs., Online Article downloaded from the site: http://www.sigmaaldrich.com/chemistry/stockroom-reagents/learning-center/technical-library/particle-size-conversion.printerview.html on Apr. 17, 2012.
Polyox Water-Soluble Resins, Technical Data, "Degradation of water-soluble resins", Form 326-00027-1002AMS (2002).
Polyox Water-Soluble Resins, Technical Data, "Water-soluble resin storage stability", Form 326-00044-0704MAB (2004).
Zhang et al., "Effect of processing methods and heat treatment on the formation of wax matrix tablets for sustained drug release", Pharm. Dev. Tech., vol. 6, No. 2, pp. 131-144 (2001).

(56) References Cited

OTHER PUBLICATIONS

Meert et al., A preclinical comparison between different opioids: antinociceptive versus adverse effects; Pharmacology, Biochemistry & Behavior; 80(2):309-Feb. 26, 2005.
Doteuchi et al., "Pharmacological Studies of Oxycodone Hydrochloride 1. Antinociceptive Effect and General Pharmacology"; Oyo Yakuri. 49(3); 1995; 257-273.
Talukder et al; "Gastroretentive Delivery Systems: A Mini Review"; Drug Development and Industrial Pharmacy; 2004; pp. 1019-1028; vol. 30, No. 10.
Hou et al; "Gastric Retentive Dosage Forms: A Review"; Critical Review in Therapeutic Drug Carrier Systems; 2003; pp. 462-497; 20(6).
Streubel et al. "Drug delivery to the upper small intestive window using gastroretentive technologies"; ScienceDirect; 2006; pp. 501-508; 6.
Streubel et al. "Gastroretentive drug delivery systems"; Expert Opin. Drug Deliv.; 2006; pp. 217-233; 3(2).
Moes, A.J.; "Gastroretentive Dosage Forms"; Critical Reviews in Therapeutic Drug Carrier Systems; 1993; pp. 143-195; 10(2).
Davis, Stanley, S.; "Formulation strategies for absorption windows"; DDT; Feb. 2005; pp. 249-257; vol. 10, No. 4.
Bardonnet et al.; "Gastroretentive dosage forms: Overview and special case of Helicobacter pylori"; Journal of Controlled Release; 2006; pp. 1-18; 111.
Miller et al. ,"Physical and chemical characteristics of some high purity magnesium stearate and palmitate powders"; Intl Journal of Pharmaceutics, 23 (1985), 55-67.
Kim, Cherng-Ju, "Effects of Drug Solubility, Drug Loading, and Polymer Molecular Weight on Drug Release from Polyox Tablets", Drug Development and Industrial Pharmacy; 24(7), (1998), 645-651.
Waterman, Kenneth, C., "A Critical Review of Gastric Retentive Controlled Drug Delivery", Pharmaceutical Development and Technology, 12:1-10, (2007).
Arora et al., "Floating Drug Delivery Systems: A Review", AAPS PharmSciTech (2005), 6(3) Article 47 E372-390.
Klausner et al., "Novel Gastroretentive Dosage Forms: Evaluation of Gastroretentivity and Its Effect on Levodopa Absorption in Humans"; Pharmaceutical Research, vol. 20, No. 9, Sep. 2003, pp. 1466-1473.
Klausner, et al., "Novel levodopa gastroretentive dosage form: in-vivo evaluation in evaluation in dogs", Journal of Controlled Release 88 (2003) 117-126.
Brzeznicka et al. "Dynamics of Glutathione Levels in Liver and Indicatory Enzymes in Serum in Acetaminophen Intoxication in Mice"(1998) Polish Journal of Occupational Medicine, vol. 2, No. 1, pp. 15-22.
Gammaitoni et al. "Radomized, Double-Blind, Placebo-Controlled Comparison of the Analgesic Efficacy of Oxycodone 10 mg/Acetaminophen 325 mg versus Controlled-Release Oxycodone 20 mg in Postsurgical Pain", (2003), J. Clin. Pharmacol, 43: pp. 296-304.
Moller et al. "Time to Onset of Analgesia and Analgesic Efficacy of Efferevescent Acetaminophen, "(2000); J. Clin. Pharmacol. 40: 370-378.
Nielsen et al. "Analgesic efficacy of immediate and sustained release paracetamol and plasma concentration of paracetamol", (1992), Eur. J. Clin Pharmacol 42: 261-264.
James et al, "Acetaminophen-Induced Hepatotoxicity", The American Society for Pharmacology and Experimental Therapeutics, (2003), vol. 31, No. 12, pp. 1499-1506.
Mirochnitchenko et al. "Acetaminophen Toxicity", The American Society for Biochemistry and Molecular Biology, Inc., (1999), vol. 274, No. 15, pp. 10349-10355.
Dart et al. "Acetaminophen Poisoning: an Evidence-Based Consensus Guideline for Out-of-Hospital Management", (2006), Clinical Toxicology; 44: pp. 1-18.
Bolesta et al. "Hepatotoxicity Associated with Chronic Acetaminophen Administration in Patients without Risk Factors", (2002), The Annals of Pharmacotherapy; Feb., 2002, vol. 36, pp. 331-333.
Rinaldi et al. "Minireview Reactive Intermediates and the Dynamics of Glutathione Transferases"(2002); The American Society for Pharmacology and Experimental Therapeutics; 30:pp. 1053-1058.
Rumack et. al. "Acetaminophen Hepatotoxicity: The First 35 Years", Clinical Toxicology, (2002); 40(1), 3-20.
Bartels et al., "Are recommended doses of acetaminophen hepatotoxic for recently abstinent alcoholics? A randomized trial"; (2008); Clinical Toxicology; 46; 243-249.
Corcoran et al. "Role of Glutathione in Prevention of Acetaminophen-Induced Hepatotoxicity by N-Acetyl-I-Cysteine in Vivo: Studies with N-Acetyl-D-Cysteine in Mice"; The Journal of Pharmacology and Experimental Therapeutics; (1986); vol. 238, No. 1; pp. 54-61.
Davis et al. "Species Differences in Hepatic Glutathione Depletion, Covalent Binding and Hepatic Necrosis after Acetaminophen", Life Sciences, vol. 14, pp. 2099-2109.
Mitchell et al. "Acetaminophen-Induced Hepatic Necrosis. IV. Protective Role of Glutathione", The Journal of Pharmacology and Experimental Therapeutics; (1973), vol. 187, No. 1, pp. 211-217.
Koplowitz et al. "Drug-Induced Liver Disease"(2003); Marcel Dekker, pp. 287-325 and pp. 345-375.
Skoglund et al. "Efficacy of paracetamol-esterified methionine versus cysteine or methionine on paracetamol-induced hepatic GSH depletion and plasma AlAT level in mice", Biochem Pharmacol 35; 3071-3075, (1986).
Khosla et al. "The effect of tablet size on the gastric emptying of non-disintegrating tablets"(1990), International Journal of Pharmaceutics, 62, R9-R11.
Khosla et al. Gastrointestinal transit of non-disintegrating tablets in fed subjects (1989), International Journal of Pharmaceutics, 53, 107-117.
Khosla et al. "The gastrointestinal transit of a controlled release formulation of indomethacin", (1990), International Journal of Pharmaceutics, 60, 191-196.

\* cited by examiner

# METHODS OF PRODUCING STABILIZED SOLID DOSAGE PHARMACEUTICAL COMPOSITIONS CONTAINING MORPHINANS

CROSS-REFERENCE TO RELATED APPLICATIONS

This patent application is a U.S. National Stage of PCT/US2011/041533, filed Jun. 22, 2011, which is a continuation-in-part of U.S. Ser. No. 12/973,962 filed 21 Dec. 2010, which claims priority to U.S. Provisional Application No. 61/284,651, filed on Dec. 22, 2009, each of is incorporated herein in its entirety.

FIELD OF THE INVENTION

The present invention relates to methods of producing stabilized solid dosage forms of morphinan pharmaceutical compositions. In particular, the present invention relates to methods of preparing morphinan-protected granules that may be incorporated into solid dosage forms of morphinan pharmaceutical compositions.

BACKGROUND OF THE INVENTION

Minimizing the degradation of active pharmaceutical ingredients (APIs) in pharmaceutical compositions is an ongoing challenge in research and development. Degradation may occur from the physical or chemical instability of the API with incompatible pharmaceutical carriers in a pharmaceutical composition, or by reactions of the API with headspace oxygen or residual water in a composition.

Oxidation is a common mechanism of API degradation in pharmaceutical compositions. The process of oxidative degradation may occur via various mechanisms such as autooxidation, nucleophilic addition, electrophilic addition, or electron transfer. Regardless of the mechanism, degradant compounds formed by the degradation of an API in a pharmaceutical composition may impart potentially harmful properties to the composition.

If degradants are present in a pharmaceutical composition above the levels prescribed by ICH Guidelines Q3A and Q3B, the degradants must undergo a qualification procedure as part of the approval process required before the use and sale of the composition is allowed. Qualification of impurities typically involves costly studies using multiple animal models, and introduces considerable risk into the development process. If degradants of a pharmaceutical composition are found to be carcinogenic or teratogenic, the composition will not gain FDA approval, diminishing the opportunity for commercialization of the API.

As a result, the process of selecting functional carriers for a pharmaceutical composition is particularly challenging. A functional pharmaceutical carrier is typically selected primarily to impart desired performance characteristics to the composition such as an extended release profile. In addition, it is desirable to select functional carriers that are chemically compatible with the API in the composition. In certain compositions, it may be necessary to incorporate functional carriers that may be incompatible with the API in order to achieve a desired performance of the API in the body. In this situation, identifying an effective means to prevent the degradation of the API is an essential part of the development of a successful therapeutic composition.

For example, the formulation of a solid dosage form of an API may incorporate a release-modifying pharmaceutical carrier in order to achieve a desired release profile after administration of the compound. Polymer carriers such as a polyethylene oxide (PEO) polymer may be incorporated into a pharmaceutical composition to impart an extended release profile to the composition. PEO polymers are produced by a process of radical polymerization process followed by oxidative degradation of the polymer to achieve the desired molecular weight. The resulting PEO polymer carriers may retain residual peroxides and other oxidative species from the production process that may cause the oxidation of the API molecules in any pharmaceutical composition that incorporates PEO polymers. Typically, other excipients such as antioxidants or pH-lowering excipients may be incorporated into the API composition to minimize the degradation of the API in the presence of incompatible carriers such as PEO polymers in the pharmaceutical composition. However, in a solid dosage form composition, this approach is less effective than in other dosage forms such as solutions or suspensions.

Morphinans, a widespread class of analgesic APIs, are particularly vulnerable to oxidative degradation, especially in compositions that incorporate PEO polymer carriers or other pharmaceutical carriers that contain residual peroxides or other oxidative species. Because the physiological effects of morphinans are notoriously sensitive to small changes in chemical structure, the formation of degradants may introduce undesirable properties to a pharmaceutical composition in which a morphinan is vulnerable to degradation. For solid dosage forms of morphinan compositions, the introduction of additional antioxidant excipients or pH-lowering excipients to prevent the degradation of the morphinan, particularly when formulated in a solid dosage form, has been relatively ineffective to date.

A need exists in the art for a method of protecting an API from degradation in a solid dose form of a pharmaceutical composition. In particular, a need exists for a method of stabilizing morphinan APIs, which are especially vulnerable to oxidative degradation, in solid dosage forms of pharmaceutical compositions.

SUMMARY OF THE INVENTION

Briefly, therefore, one aspect of the disclosure provides a method for the preparation of a solid dosage form pharmaceutical composition comprising a morphinan and at least one other active pharmaceutical ingredient. The method comprises three steps. In the first step, a mixture comprising the morphinan and at least one excipient is granulated in a manner such that the amount of morphinan exposed on the surface of the granule is substantially reduced thereby forming a morphinan-protected granule. The second step comprises granulating a mixture comprising the morphinan-protected granule, the active pharmaceutical agent, and at least one excipient to form a granulated mixture. In the third step, the granulated mixture is blended with a release-controlling polymer comprising a polyethylene oxide polymer to form the solid dosage form pharmaceutical composition comprising a sustained release layer.

In another aspect of the disclosure, a method for the preparation of a solid dosage form pharmaceutical composition comprising oxycodone and acetaminophen is provided. The method comprises three steps. In the first step, a mixture comprising the oxycodone and at least one excipient is granulated in a manner such that the amount of oxycodone exposed on the surface of the granule is substantially reduced thereby forming an oxycodone-protected granule. In the next step, a mixture comprising the oxycodone-protected granule, the acetaminophen, and at least one excipient is granulated to form a granulated mixture. The third step comprises blending the granulated mixture with a release-controlling polymer comprising a polyethylene oxide polymer is granulated to form the solid dosage form pharmaceutical composition comprising a sustained release layer.

An additional aspect of the disclosure provides a method for the preparation of a bilayer tablet comprising a sustained release layer and an immediate release layer. The method comprises four steps. In a first step, a mixture comprising oxycodone or hydrocodone and at least one excipient is granulated in a manner such that the amount of oxycodone or hydrocodone exposed on the surface of granule is substantially reduced thereby forming a morphinan-protected granule. In the next step, a mixture comprising the morphinan-protected granule, the acetaminophen, and at least one excipient is granulated to form a granulated mixture. In the third step, the granulated mixture is blended with a release-controlling polymer comprising a polyethylene oxide polymer to form a sustained release layer. In the final step, a mixture comprising the morphinan-protected granule from the first step is granulated with the acetaminophen and at least one excipient to form the immediate release layer.

A further aspect of the disclosure encompasses a granule that is substantially resistant to oxidative degradation of oxycodone. The granule comprises an interior region substantially comprising oxycodone that is surrounded by an exterior region substantially comprising at least one excipient. Moreover, the granule contains less than about 0.5% w/w of the total mass of oxycodone of a degradant selected from 10-hydroxy oxycodone, di-hydroxy oxycodone, and oxycodone n-oxide after being stored for 6 months at 40° C. and 75% relative humidity.

Another aspect of the disclosure provides a granule substantially resistant to oxidative degradation of hydrocodone. The granule comprises an interior region substantially comprising hydrocodone that is surrounded by an exterior region substantially comprising at least one excipient, wherein the granule contains less than about 0.5% w/w of the total mass of hydrocodone of a degradant selected from hydrocodone-n-oxide and hydrocodone aldol dimer after being stored for 6 months at 40° C. and 75% relative humidity.

Yet another aspect of the disclosure provides a granule substantially resistant to oxidative degradation of a morphinan, the granule prepared by a process comprising granulating a mixture comprising the morphinan and at least one excipient in a manner such that the amount of morphinan exposed on the surface of the granule is substantially reduced thereby forming the morphinan-protected granule.

An additional aspect of the disclosure encompasses a pharmaceutical composition comprising a plurality of oxycodone-containing granules substantially resistant to oxidative degradation of oxycodone and at least one pharmaceutically acceptable carrier. The plurality of granules comprise an interior region substantially comprising oxycodone that is surrounded by an exterior region substantially comprising at least one excipient, wherein the granule contains less than about 0.5% w/w of the total mass of oxycodone of a degradant selected from 10-hydroxy oxycodone, di-hydroxy oxycodone, and oxycodone n-oxide after being stored for 6 months at 40° C. and 75% relative humidity.

Another aspect of the disclosure provides a pharmaceutical composition comprising a plurality of hydrocodone-containing granules substantially resistant to oxidative degradation of hydrocodone and at least one pharmaceutically acceptable carrier. The plurality of granules comprise an interior region substantially comprising hydrocodone that is surrounded by an exterior region substantially comprising at least one excipient, wherein the granule contains less than about 0.5% w/w of the total mass of hydrocodone of a degradant selected from hydrocodone n-oxide and hydrocodone aldol dimer after being stored for 6 months at 40° C. and 75% relative humidity.

Yet another aspect provides a solid dosage pharmaceutical composition comprising a plurality of oxycodone-protected granules and acetaminophen, the composition prepared by a process comprising (a) granulating a mixture comprising the oxycodone and at least one excipient in a manner such that the amount of oxycodone exposed on the surface of the granule is substantially reduced thereby forming the plurality of oxycodone-protected granules; (b) granulating a mixture comprising the plurality of oxycodone-protected granules, the acetaminophen, and at least one excipient to form a granulated mixture; and (c) blending the granulated mixture with a release-controlling polymer comprising a polyethylene oxide polymer to form the solid dosage form the pharmaceutical composition comprising a sustained release layer.

Other features and iterations of the invention are described in more detail below.

DETAILED DESCRIPTION

The invention provides methods of preparing morphinan-protected granules by combining a morphinan with at least one excipient to form a mixture, and granulating the mixture. The resulting morphinan-protected granules have a physical structure that minimizes the amount of morphinan that is exposed on the surface of the granule. The morphinan-protected granules may stabilize the morphinan against various mechanisms of degradation such as oxidation by substantially decreasing the amount of morphinan exposed on the surface of the granule thereby reducing the degree of contact between the morphinan and the oxidative species in the environment surrounding the granules, including but not limited to carriers and residual water in the composition, and atmospheric oxygen and moisture.

In addition, if chemically protective excipients including but not limited to antioxidants and pH-adjusting agents are included in the excipient mixture forming the morphinan-protected granule, the morphinan contained within the granule is further protected against degradation. Any oxidative species contained in the environment surrounding the morphinan-protected granules may react with the chemically protective excipients situated the granules before they can reach the morphinan.

The morphinan-protected granules may be prepared using any device known in the art, including but not limited to a high-shear wet granulator. The particular device used for granulation may affect the physical properties of the resulting granules, including but not limited to granule size, granule density, and granule porosity, all of which may influence the protective properties of the granule against degradation of the morphinan. Regardless of the granulation method used to form the granules, the distribution of morphinan and excipients within the granules is influenced by at least several factors including but not limited to the size of the morphinan particles relative to the excipient particles in the mixture prior to granulation, the chemical properties of the morphinan and excipients including but not limited to hydrophobicity and ionic charge, and the presence of excipients dissolved in the granulation solution used to prepare the granules.

The morphinan-protected granules prepared by the methods of the invention may be incorporated into a solid dose form of a pharmaceutical composition, including but not limited to tablet and capsule formulations. In addition to protection against degradation, the inclusion of the morphinan in the form of granules imparts several other advantageous aspects to the resulting composition. Because the morphinan in the granules is protected, the choice of carrier may be selected to satisfy constraints other than compatibility with the morphinan. Carriers in the composition may instead be selected based on factors including but not limited to the cost of the carrier, the desirable modified-release properties imparted by a particular carrier. Further, variation in the characteristics of the morphinan-protected granules including granule size, excipients included in the granules, and the physical structure of the granules may be used to control the release profile or other pharmacokinetic characteristics of pharmaceutical compositions.

Detailed descriptions of various embodiments of the morphinan protected granules, methods of preparing the morphinan protected granules, and solid dosage forms of pharmaceutical compositions that include the morphinan-protected granules are described in detail below.

(I) Morphinan-Protected Granules

The granules prepared by the methods of the invention stabilize the morphinan contained within the granules by substantially reducing the amount of morphinan exposed on the surface of the granule. In this regard, significantly less of the morphinan is in contact with any oxidative species in the environment outside of the granule, and may additionally provide chemical protection of the morphinan against degradation by surrounding the morphinan with chemically protective excipients including but not limited to antioxidants that are contained within the morphinan-protected granule. The physical structure of the morphinan-protected granule may influence the protective efficacy of the granule against degradation of the morphinan, and further influences the suitability of the granules for inclusion in various solid dose forms of pharmaceutical compositions, including but not limited to tablets and capsules.

(a) Granule Structure

The physical structure of the granule includes the morphinan dispersed within the excipient mixture and granulated in a manner such that the amount of morphinan exposed on the surface of the granule is substantially reduced. The particular physical structure of any embodiment of a morphinan-protected granule is influenced by at least several factors related to the method of preparing the granules and the particular morphinan and excipients included in the granule. The influence of these factors on the physical structure of the granules is described in detail below.

In general, the physical structure of the granules may vary from an essentially random spatial distribution of the morphinan and excipients throughout the granules to a highly ordered distribution in which essentially all of the morphinan is contained within a sharply delineated interior region that is surrounded by an exterior region that contains essentially all of the excipients. In an embodiment, the amount of morphinan that is exposed at the surface of the granules is less than about 100% of the total weight of the morphinan in the granules. In other embodiments, the amount of morphinan that is exposed at the surface of the granules is less than about 95%, less than about 90%, less than about 80%, less than about 70%, less than about 60%, less than about 50%, less than about 40%, less than about 30%, less than about 20%, less than about 10%, and less than about 5% of the total weight of morphinan in the granule.

Excipients contained within the granule may provide additional protection against degradation of the morphinan by chemically interacting with degradative compounds surrounding or within the granule. For example, the effectiveness of the excipients at protecting the morphinans in the granule may be enhanced if at least one of the excipients includes but is not limited to an antioxidant, a chelating agent, or a pH-adjusting agent. Various embodiments of the excipients included in the granule are described in detail below.

The density and porosity of the exterior regions of the granules may influence the effectiveness of the exterior regions at protecting the morphinans in the granules from degradation. Exterior regions having higher densities and lower porosities may be more resistant to penetration by degradative compounds from outside the granule. The densities and porosities of the exterior regions of the granules may be influenced by at least several factors including but not limited to the particular morphinan and excipients included in the granule and the device used to prepare the granule. For example, a granule prepared using a high-shear wet granulator may have a higher density and lower porosity compared to a granule with a similar composition prepared using a fluid bed granulator.

The $d_{90}$ of the granules in various embodiments may be selected based on the intended use of the granules, in particular the particular solid dosage form in which the granules are to be incorporated. The particular $d_{90}$ of the granule may be influenced by a variety of factors including but not limited to the composition of the granule and the granulation device used to prepare the granules. The $d_{90}$ of the granules may be larger for granule compositions having a higher proportion of excipients including but not limited to binders and fillers relative to other types of excipients.

In various embodiments, the granules may have an average $d_{90}$ of less than about 2000 µm. In other embodiments, the granules may have an average $d_{90}$ of less than about 1800 µm, less than about 1500 µm, less than about 1000 µm, less than about 900 µm, less than about 800 µm, less than about 700 µm, less than about 600 µm, less than about 500 µm, less than about 400 µm, less than about 300 µm, less than about 200 µm, less than about 150 µm, and less than about 100 µm. In one exemplary embodiment in which the granules are to be incorporated in a solid dosage form including but not limited to a capsule, the granules may be less than about 1000 µm in average $d_{90}$. In another exemplary embodiment in which the granules are to be incorporated in a solid dosage form including but not limited to a tablet, the granules may be less than about 800 µm in average $d_{90}$. In yet another embodiment, the granules may range from about 150 µm to about 200 µm in average $d_{90}$.

(II) Granule Composition

The composition of the granules prepared using the methods of the invention include a morphinan and at least one excipient. The particular composition of the granules may influence a variety of properties of the granules including but not limited to the physical structure of the granules, the stability of the morphinan contained within the granule, and the suitability of the granules for incorporation into a particular dry dosage form of a pharmaceutical composition.

One aspect of the composition that may influence the physical structure of the granules is the $d_{90}$ of the morphinan particles relative to the $d_{90}$ of the excipient particles in the mixture that used to form the granules. As used herein, $d_{90}$ represents the particle diameter at which 90% of the individual particles of a compound are smaller than the specified diameter. Without being bound to any particular theory, when a granulation device including but not limited to a low-shear wet granulator, a high-shear wet granulator, or a fluid bed granulator is used to granulate the mixture of the morphinan and at least one excipient, the compounds having a smaller $d_{90}$ relative to the other compounds in the mixture tend to aggregate near the interior regions of the granules, and the compounds having larger $d_{90}$ tend to aggregate near the exterior regions of the granules, regardless of whether the compound is a morphinan or an excipient.

As a practitioner skilled in the art may appreciate, for granule compositions in which the morphinan accounts for an extremely low proportion of the total mass of the granule, the size of the morphinan particles relative to the excipient particles may not exert the same influence on the physical structure of the resulting granules as described previously. By way of a non-limiting example, if a granule is prepared using a mixture containing about 5% morphinan and about 95% excipients by weight, and the $d_{90}$ of the morphinan is larger than the $d_{90}$ of the excipients, the relative scarcity of the morphinan particles may result in a granule in which the individual morphinan particles are surrounded by excipient particles, and the morphinan particles may be located in both the interior region and the exterior region of the granule.

In one embodiment, the $d_{90}$ of the morphinan is smaller than the $d_{90}$ of the excipients. In another embodiment, the $d_{90}$ of the morphinan is less than about 80% of the $d_{90}$ of the excipients. In yet other embodiments, the $d_{90}$ of the morphinan is less than about 75%, less than about 70%, less than about 65%, less than about 60%, less than about 55%, or less than about 50% of the $d_{90}$ of the excipients.

The $d_{90}$ values of the morphinan and the excipients may also be influenced by the capabilities of the particular device used to prepare the granules. Without being bound to any particular theory, when a granulation device including but not limited to a low-shear wet granulator, a high-shear wet granulator, or a fluid bed granulator is used to granulate the mixture of the morphinan and at least one excipient, if the $d_{90}$ of a particular compound falls below a threshold $d_{90}$, the particles of that compound tend to aggregate before they are granulated, resulting in granules that have a non-homogenous distribution of the compound from granule to granule.

In other embodiments, other properties of the morphinan and excipients may influence the physical structure of the granule including but not limited to the hydrophobicity and ionic charge of the morphinan relative to the one or more excipients. As a non-limiting illustrative example, if the morphinan is hydrophobic relative to the excipients and if a polar granulation fluid is used in the granulation process, hydrophobic repulsive forces may tend to situate the morphinan within the interior region of the granules.

In one embodiment, the composition of the granules includes one morphinan compound. In other embodiments, the composition of the granules may further include one or more additional morphinan compounds within each granule. Any number of different morphinans may be included in the composition of the granules, so long as all morphinans that are included in the granule are physically and chemically compatible.

An acid, as defined herein, refers to the acid and any pharmaceutically acceptable salt of the acid.

(a) Morphinans

The compositions of various embodiments of the granules include a morphinan. In one embodiment, the morphinan may be included in the granules in an amount of up to about 90% of the total weight of the granules. In other embodiments, the morphinan may be included in the granules in an amount ranging up to about 80%, up to about 70%, up to about 60%, up to about 50%, up to about 40%, up to about 30%, up to about 20%, up to about 10%, up to about 1%, and up to about 0.5% of the total weight of the granules.

The morphinan included in various embodiments of the granules may be selected from opium, natural opium derivatives, semi-synthetic opium derivatives, and synthetic opium derivatives. Non-limiting examples of suitable morphinans for various embodiments of the granules include adlumine, allocryptopine, aporphine, benzylmorphine, berberine, biculine, bicucine, bulbocapnine, buprenorphine, butorphanol, canadine, capaurine, chelerythrine, chelidonine, coda mine, codeine, coptisine, corexamine, corlumine, corybulbine, corycavamine, corycavine, corydaline, corydine, corytuberine, cularine, cotamine, cryptopine, cycloartenol, cycloartenone, cyclolaudenol, dehydroreticuline, desomorphine, dextropropoxyphene, dextrorphanol, diacetylmorphine, dicentrine, dihydrosanguinarine, dipropanoylmorphine, epiporphyroxine, ethylmorphine, eupaverine, fagarine, fentanyl, glaucine, homochelidonoine, hydrocodone, hydrocotamine, hydromorphone, hydroxythebaine, isoboldine, isocorybulbine, isocorydine, isocorypalmine, isoquinoline, laudanidine, laudanine, laudanosine, levorphanol, magnoflorine, meconic acid, methadone, morphine, nalbuphine, nalmefene, naloxone, naltrexamine, α-naltrexol, β-naltrexol, naltrexone, naphthaphenanthridine, narceine, narceinone, narcotoline, narcotise, neopine, nicomorphine, norlaudanosoline, norsanguinarine, noscapine, opium, oripavine, oxycodone, oxymorphone, oxysanguinarine, palaudine; papaverine, papaveraldine, papaverrubine, perparin, pethidine, phenanthrene, phtalide-isoquinoline, porphyroxine, protopine, pseudocodeine, pseudomorphine, reticuline, salutaridine, sinoacutine, sanguinarine, scoulerine, somniferine, stepholidine, tapentadol, tetrahydroprotoberberine, thebaine, tramadol, and xanthaline. In an exemplary embodiment, the morphinan included in the granules may be selected from oxycodone, oxymorphone, hydrocodone, hydromorphone, nalbuphine, naloxone, buprenorphine, and naltrexone. In another exemplary embodiment, the morphinan in the granules is oxycodone or hydrocodone.

Any of the morphinans included in the embodiments of the granules may have a (−) or (+) orientation with respect to the rotation of polarized light, depending upon whether the starting substrate has (−) or (+) optical activity, and are referred to herein as (−)-morphinans and (+)-morphinans respectively. More specifically, each chiral center may independently have an R or an S configuration.

As an illustrative example, an embodiment of the granules may include a morphinan compound possessing a fused carbon ring structure. The ring atoms of the morphinan compound may be numbered as diagrammed in Formula (I) below. Morphinan compounds have asymmetric centers and the core morphinan compound may have at least four chiral carbons including but not limited to C-5, C-13, C-14, and C-9. In various embodiments, the configuration of the chiral carbons C-5, C-13, C-14, and C-9 may be RRRR, RRSR, RRRS, RRSS, RSRR, RSSR, RSRS, RSSS, SRRR, SRSR, SRRS, SRSS, SSRR, SSSR, SSRS, or SSSS, provided that the C-15 and the C-16 carbons are both oriented either on the alpha face or the beta face of the morphinan molecule.

(I)

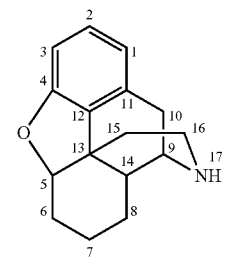

In various embodiments of the granules, the morphinan may be provided in any solid form including but not limited to a finely divided solid, a crystal, a particle, a powder, or any other finely divided solid form known in the art. Any finely divided solid form of the morphinan may be used so long as the $d_{90}$ of the morphinan particles are smaller than the $d_{90}$ of the one or more excipients as described above.

(b) Excipients

Various embodiments of the granules include one or more excipients in addition to the morphinan. In general, the one or more excipients are selected to impart at least one or more desired physical or chemical properties to the granules, including but not limited to adhesion of the particles of the morphinan and excipient compounds in the mixture to facilitate the formation of granules, formation of physical barriers around the morphinans in the granules, and chemical inhibition of various mechanisms of degradation of the morphinans including but not limited to oxidation. Non-limiting examples of the one or more excipients include binders, fillers, antioxidants, pH-adjusting agents, chelating agents, and antimicrobial agents.

In one embodiment, the one or more excipients may be introduced into the mixture to be granulated in a solid form including but not limited to a crystal, a particle, a powder, or any other finely divided solid form known in the art. In another embodiment, the one or more excipients may be dissolved or suspended in a solvent and sprayed onto the mixture in a granulation device as a binder fluid during granulation.

(i) Binders

In general, binders are excipients included in various embodiments of the granule to impart structural integrity to the granules by binding together the particles making up each granule. Non-limiting examples of binders suitable for the formulations of various embodiments include starches, pregelatinized starches, gelatin, polyvinylpyrrolidone, cellulose, methylcellulose, sodium carboxymethylcellulose, ethylcellulose, polyacrylamides, polyvinyloxoazolidone, polyvinylalcohols, C12-C18 fatty acid alcohols, polyethylene glycol, polyols, saccharides, oligosaccharides, polypeptides, oligopeptides, and combinations thereof. The polypeptides may be any arrangement of amino acids ranging from about 100 to about 300,000 Daltons.

In one embodiment, the binder may be introduced into the mixture to be granulated in a solid form including but not limited to a crystal, a particle, a powder, or any other finely divided solid form known in the art. In another embodiment, the binder may be dissolved or suspended in a solvent and sprayed onto the mixture in a granulation device as a binder fluid during granulation.

(ii) Fillers

Fillers may be included in various embodiments of the granule composition as an excipient to increase the bulk volume of the granules and to impart suitable compressibility characteristics to the granules for subsequent inclusion in solid dosage forms of pharmaceutical compositions including but not limited to tablets. Non-limiting examples of fillers include carbohydrates, inorganic compounds, and polyvinylpyrrolidone. Other non-limiting examples of fillers include dibasic calcium sulfate, tribasic calcium sulfate, starch, calcium carbonate, magnesium carbonate, microcrystalline cellulose, dibasic calcium phosphate, tribasic calcium phosphate, magnesium carbonate, magnesium oxide, calcium silicate, talc, modified starches, lactose, sucrose, mannitol, and sorbitol.

(iii) Antioxidants

Antioxidants are excipients included in various embodiments of the granules to prevent the oxidation of the morphinan in the granules. Suitable antioxidants include, but are not limited to anoxomer, N-acetylcysteine, benzyl isothiocyanate, m-aminobenzoic acid, o-aminobenzoic acid, p-aminobenzoic acid (PABA), butylated hydroxyanisole (BHA), butylated hydroxytoluene (BHT), caffeic acid, canthaxantin, alpha-carotene, beta-carotene, beta-caraotene, beta-apo-carotenoic acid, carnosol, carvacrol, catechins, chlorogenic acid, citric acid and its salts, clove extract, coffee bean extract, p-coumaric acid, 3,4-dihydroxybenzoic acid, N,N'-diphenyl-p-phenylenediamine (DPPD), dilauryl thiodipropionate, distearyl thiodipropionate, 2,6-di-tert-butylphenol, edetic acid, ellagic acid, erythorbic acid, sodium etythorbate, esculetin, esculin, 6-ethoxy-1,2-dihydro-2,2,4-trimethylquinoline, ethyl maltol, ethylenediaminetetraacetic acid (EDTA) and EDTA salts, eucalyptus extract, eugenol, ferulic acid, flavonoids (e.g., catechin, epicatechin, epigallocatechin (EGC), flavones (e.g., apigenin, chrysin, luteolin), flavonols (e.g., datiscetin, myricetin, daemfero), flavanones, fraxetin, fumaric acid, gallic acid, gentian extract, gluconic acid, glycine, gum guaiacum, hesperetin, alpha-hydroxybenzyl phosphinlc acid, hydroxycinammic acid, hydroxyglutaric acid, hydroquinone, N-hydroxysuccinic acid, hydroxytryrosol, hydroxyurea, rice bran extract, lactic acid and its salts, lecithin, lecithin citrate; R-alpha-lipoic acid, lutein, lycopene, malic acid, maltol, 5-methoxy tryptamine, monoglyceride citrate, monoisopropyl citrate; morin, beta-naphthoflavone, nordihydroguaiaretic acid (NDGA), oxalic acid, palmityl citrate, phenothiazine, phosphatidylcholine, phosphoric acid, phosphates, phytic acid, phytylubichromel, pimento extract, polyphosphates, quercetin, trans-resveratrol, rosemary extract, rosmarinic acid, sage extract, sesamol, silymarin, sinapic acid, succinic acid, stearyl citrate, syringic acid, tartaric acid, thymol, tocopherols (i.e., alpha-, beta-, gamma- and delta-tocopherol), tocotrienols (i.e., alpha-, beta-, gamma- and delta-tocotrienols), tyrosol, vanilic acid, 2,6-di-tert-butyl-4-hydroxymethylphenol (i.e., Ionox 100), 2,4-(tris-3',5'-bi-tert-butyl-4'-hydroxybenzyl)-mesitylene (i.e., Ionox 330), 2,4,5-trihydroxybutyrophenone, ubiquinone, tertiary butyl hydroquinone (TBHQ), thiodipropionic acid, trihydroxy butyrophenone, tryptamine, tyramine, uric acid, vitamin K and derivates, vitamin Q10, wheat germ oil, zeaxanthin, or combinations thereof.

In another embodiment, an antioxidant agent may be subjected to a particle size reduction process including but not limited to grinding, milling, sonication, or hammer milling in order to reduce the $d_{90}$ of the antioxidant agent to a value less than the $d_{90}$ of the morphinan (or other API included in the formulation) prior to granulation. In this embodiment, the reduced $d_{90}$ of the antioxidant agent may result in a distribution of antioxidant agent that is clustered around the morphinan particles, rather than near the outer surface of the granule. A granule having this physical structure may provide comparable protection of the morphinan in the granules against degradation as compared to granules in which the antioxidant agent is situated on the outside of the granule using a significantly lower amount of the antioxidant agent.

In an exemplary embodiment, the granule composition includes at least one antioxidant including but not limited to citric acid and Na$_2$EDTA.

(iv) pH-Adjusting Agents

In various embodiments of the granule composition, a pH-adjusting agent may be included as an excipient to raise or lower the pH of the granule in order to prevent the oxidation of the morphinan in the granules. For example, a pH-adjusting agent including but not limited to citric acid may be incorporated into the composition granule in order to lower the pH of the granule. In this example, a lower pH prevents the oxidation of the granule by various oxidative compounds associated with release-modifying polymer incorporated into a sold dosage form, including but not limited to peroxides.

In another embodiment, a pH-adjusting agent may be subjected to a particle size reduction process including but not limited to grinding, milling, sonication, or hammer milling in order to reduce the $d_{90}$ of the pH-adjusting agent to a value less than the $d_{90}$ of the morphinan prior to granulation. In this embodiment, the reduced $d_{90}$ of the pH-adjusting agent may result in a distribution of pH-adjusting agent that is clustered around the morphinan particles, rather than near the outer surface of the granule. Non-limiting examples of pH-adjusting agents include citric acid, acetic acid, tartaric acid, malic acid, fumaric acid, lactic acid, phosphoric acid, sorbic acid, benzoic acid, sodium carbonate and sodium bicarbonate.

(v) Chelating Agents

In various embodiments of the granule composition, a chelating agent may be included as an excipient to immobilize oxidative species including but not limited to metal ions in order to inhibit the oxidative degradation of the morphinan by these oxidative species. Non-limiting examples of chelating agents include lysine, methionine, glycine, gluconate, polysaccharides, glutamate, aspartate, and $Na_2EDTA$.

(vi) Antimicrobial Agents

In various embodiments of the granule composition, an antimicrobial agent may be included as an excipient to minimize the degradation of the morphinan by microbial agents including but not limited to bacteria and fungi. Non limiting examples of antimicrobials include parabens, chlorobutanol, phenol, calcium propionate, sodium nitrate, sodium nitrite, $Na_2EDTA$ and sulfites including but not limited to sulfur dioxide, sodium bisulfite, and potassium hydrogen sulfite.

(III) Granule Stability

In various embodiments of the granule composition, the morphinan in the granule is substantially resistant to degradation due to interactions of the morphinan with degradative compounds or conditions present in the environment or in the carriers surrounding the granules in a solid dosage form of a pharmaceutical composition. In one embodiment, the morphinan in the granules is substantially resistant to the formation of degradants resulting from a chemical change in the morphinan brought about during the production and/or storage of the pharmaceutical composition containing the morphinan by the effect of factors including but not limited to light, temperature, pH, water, or reaction with an excipient or carrier included in the pharmaceutical composition. The particular degradants formed in a pharmaceutical composition depend on the particular morphinan and the at least one excipient within the granule, as well as the particular carriers included in the pharmaceutical composition along with the granules.

Statutory requirements, including but not limited to ICH Guidelines Q3A and Q3B identify maximum allowable amounts of degradants above which the degradants must be reported and subjected to the qualification process described above. According to ICH Guideline Q3B, the amount of any individual degradant must be reported if the amount of degradant exceeds 0.10% of the total API weight for maximum daily doses of 1000 mg of API or below. For APIs having average daily doses of above 1000 mg, degradants in excess of 0.05% of the total API mass must be reported. The ICH guidelines apply throughout the effective shelf life of the pharmaceutical composition.

Although no standardized method of assessing API stability exists at present, drug developers typically subject potential pharmaceutical compounds to periods of storage at accelerated degradation conditions, typically defined as a temperature of about 40° C. and a relative humidity of about 75%. The period of storage time at the accelerated degradation conditions may vary from about 1 day to about 6 months, but is typically about 6 months. In an embodiment, the formation of any one degradant in the composition may be limited to less than about 0.5%, less than about 0.4%, less than about 0.3%, less than about 0.2%, less than about 0.1%, less than 0.05%, less than 0.04%, less than 0.03%, less than 0.02%, or less than 0.01% of the total mass of the morphinan after about two months of storage at a temperature of about 40° C. and a relative humidity of about 75%. In another embodiment, the formation of any one degradant in the composition may be limited to less than about 0.5%, less than about 0.4%, less than about 0.3%, less than about 0.2%, less than about 0.1%, less than 0.05%, less than 0.04%, less than 0.03%, less than 0.02%, or less than 0.01% of the total mass of the morphinan after about six months of storage at a temperature of about 40° C. and a relative humidity of about 75%. In yet another embodiment, the formation of any one degradant in the composition may be limited to less than about 0.5%, less than about 04%, less than about 0.3%, less than about 0.2%, less than about 0.1%, less than 0.05%, less than 0.04%, less than 0.03%, less than 0.02%, or less than 0.01% of the total mass of the morphinan after about four weeks of storage at accelerated stability conditions at a temperature of about 40° C. and a relative humidity of about 75%.

In an exemplary embodiment, for a pharmaceutical composition incorporating oxycodone as the morphinan and at least one excipient in the form of granules, the granules contain less than about 0.5% w/w of the total mass of oxycodone of a degradant selected from 10-hydroxy oxycodone, di-hydroxy oxycodone, and oxycodone n-oxide after being stored for 6 months at 40° C. and 75% relative humidity. In another exemplary embodiment, for a pharmaceutical composition incorporating oxycodone and at least one excipient in the form of granules, the granules contain less than about 0.5% w/w of the total mass of oxycodone of each of one or more degradants selected from 10-hydroxy oxycodone, di-hydroxy oxycodone, and oxycodone n-oxide after being stored for 6 months at 40° C. and 75% relative humidity.

In another exemplary embodiment, for a pharmaceutical composition incorporating hydrocodone as the morphinan and at least one excipient in the form of granules, the granules contain less than about 0.5% w/w of the total mass of hydrocodone of a degradant selected from hydrocodone n-oxide and hydrocodone aldol dimer after being stored for 6 months at 40° C. and 75% relative humidity. In another exemplary embodiment, for a pharmaceutical composition incorporating hydrocodone and at least one excipient in the form of granules, the granules contain less than about 0.5% w/w of the total mass of hydrocodone of each of one or more degradants selected from hydrocodone n-oxide and hydrocodone aldol dimer after being stored for 6 months at 40° C. and 75% relative humidity (IV) Method of Preparing Granules In various embodiments, the granules may be prepared by combining the morphinan with at least one excipient to form a mixture and granulating the mixture in a manner such that the amount of morphinan exposed on the surface of the granules is minimized (thereby forming a morphinan-protected granule).

Suitable morphinans for the granule embodiments are described in detail in Section (IIa) above, and suitable excipients are described in Section (IIb) above. The mixture may be formed using any suitable method known in the art including but not limited to stirring, shaking, vibrating, and blending. In an embodiment, the morphinan and dry excipients may be charged into a granulation device and mixed prior to the addition of the granulation fluid.

Any suitable granulation device known in the art may be used to prepare the granules. As previously discussed, the particular granulation device selected for the preparation of the granules may influence the physical properties of the resulting granules. Non-limiting examples of suitable devices for the preparation of the granules include a low-shear wet granulator, a high-shear wet granulator, a fluid-bed granulator, a roller compactor, a vertical granulator, an oscillating granulator, a gelatinizer, a pelletizer, and a spheronizer. The granulation device may be selected in order to prepare granules having the desired granule physical characteristics described in Section (II) above.

In an exemplary embodiment, a high-shear wet granulator is used to prepare the granules. The high-shear wet granulator may be capable of preparing granules having properties that enhance the protective effect of the granule, including but not limited to higher granule densities and lower granule porosities relative to granules prepared by other devices. Further, the high-shear wet granulator is capable of preparing granules with a $d_{90}$ that is larger than other granulation devices, resulting in granules suitable for inclusion in a wider variety of solid dosage forms of morphinan compositions.

In the same exemplary embodiment, the morphinan and the excipients in dry form of the composition are introduced into the wet high shear granulator in order to form the mixture. After the morphinan and the dry excipients are essentially homogeneously distributed within the granulator, a granulation fluid is sprayed into the granulator. In various embodiments, the granulation fluid may be any volatile, non-toxic granulation fluid known in the art. Non-limiting examples of suitable granulation fluids include water, ethanol, isopropanol, and combinations thereof. In other embodiments, one or more of the excipients may be mixed with the granulation fluid prior to spraying the granulation fluid into the granulator. In an exemplary embodiment, a binder including but not limited to pregelatinized starch may be dissolved into the granulation fluid including but not limited to water to form a granulation solution, and the granulation solution may be sprayed into the granulator in order to prepare the granules.

In an additional embodiment, the wet granules prepared in the high shear wet granulator may be dried using a drying device, resulting in dried granules having a water content of less than about 5%, less than about 4%, less than about 3%, or less than about 2% of the total weight of the granules. Any suitable drying device known in the art may be used to dry the wet granules, including but not limited to an oven, a vacuum oven, and a rotary drum dryer.

(V) Solid Dosage Forms Incorporating Granules

The morphinan-protected granules prepared by various embodiments may be incorporated into various solid dosage pharmaceutical compositions. Non-limiting examples of solid dosage pharmaceutical compositions incorporating embodiments of the morphinan granules include granules, tablets, and capsules. Non-limiting embodiments of tablets include uncoated tablets, coated tablets, mini-tablets, orally disintegrating tablets, and bilayer tablets. Non-limiting embodiments of capsules include hard capsules and multilayer capsules. Depending on the selection of particular formulation, the solid dosage pharmaceutical composition may have release characteristics including but not limited to rapid release, sustained release, extended release, slow release, time release, and combinations thereof.

In an exemplary embodiment, solid dosage form pharmaceutical compositions are made via a two step process. First, the morphinan-protected granule is formed. The morphinan-protected granule is then mixed with excipients and other active pharmaceutical ingredients, which are then granulated to form the solid dosage form pharmaceutical composition. The solid dosage form pharmaceutical composition may include additional APIs. In an exemplary embodiment, the solid dosage form pharmaceutical composition comprises a morphinan and acetaminophen. In additional embodiments, the solid dosage form pharmaceutical composition may comprise sustained release (SR) and immediate release layers (IR). Typically, the SR and IR layers both include the morphinan and acetaminophen. In each of the foregoing embodiments, the SR layer typically comprises a release-controlling polymer comprising a polyethylene oxide polymer.

(a) Compositions of Solid Dosage Forms

Various embodiments of the solid dosage pharmaceutical compositions incorporating the morph man-protected granules may include one or more pharmaceutically acceptable carriers in addition to the granules. Pharmaceutically acceptable carriers suitable for embodiments of the solid dosage pharmaceutical compositions may include but are not limited to binders, fillers, lubricants, diluents, non-effervescent disintegrants, effervescent disintegrants, flavor-modifying agents, sweeteners, dispersants, coloring agents, taste masking agents, release-controlling polymers and combinations thereof.

(i) Binders

Non-limiting examples of binders suitable for the formulations of various embodiments include starches, pregelatinized starches, gelatin, polyvinylpyrrolidone, cellulose, hydroxypropyl methylcellulose, hydroxypropyl cellulose, methylcellulose, sodium carboxymethylcellulose, ethylcellulose, polyacrylamides, polyvinyloxoazolidone, polyvinylalcohols, C12-C18 fatty acid alcohols, polyethylene glycol, polyols, saccharides, oligosaccharides, polypeptides, oligopeptides, and combinations thereof. The polypeptide may be any arrangement of amino acids ranging from about 100 to about 300,000 Daltons.

(ii) Fillers

Non-limiting examples of fillers include carbohydrates, inorganic compounds, and polyvinylpyrrolidone. Other non-limiting examples of fillers include dibasic calcium sulfate, tribasic calcium sulfate, starch, calcium carbonate, magnesium carbonate, microcrystalline cellulose, dibasic calcium phosphate, tribasic calcium phosphate, magnesium carbonate, magnesium oxide, calcium silicate, talc, modified starches, lactose, sucrose, mannitol, and sorbitol.

(iii) Lubricants

Non-limiting examples of lubricants include magnesium stearate, calcium stearate, zinc stearate, hydrogenated vegetable oils, sterotex, polyoxyethylene monostearate, talc, polyethylene glycol, sodium benzoate, sodium lauryl sulfate, magnesium lauryl sulfate, and light mineral oil.

(iv) Diluents

Diluents suitable for use include but are not limited to pharmaceutically acceptable saccharides such as sucrose, dextrose, lactose, microcrystalline cellulose, fructose, xylitol, and sorbitol; polyhydric alcohols; starches; pre-manufactured direct compression diluents; and mixtures of any of the foregoing.

(v) Non-Effervescent and Effervescent Disintegrants

Non-limiting examples of non-effervescent disintegrants include starches such as corn starch, potato starch, pregelatinized and modified starches thereof, sweeteners, clays, such as bentonite, micro-crystalline cellulose, alginates, sodium starch glycolate, gums such as agar, guar, locust bean, karaya, pecitin, and tragacanth. Suitable effervescent disintegrants include but are not limited to sodium bicarbonate in combination with citric acid, and sodium bicarbonate in combination with tartaric acid.

(vi) Flavor-Modifying Agents

Suitable flavor-modifying agents include but are not limited to synthetic flavor oils and flavoring aromatics and/or natural oils, extracts from plants, leaves, flowers, fruits, and combinations thereof. Other non-limiting examples of flavor-modifying agents include cinnamon oils, oil of wintergreen, peppermint oils, clover oil, hay oil, anise oil, eucalyptus, vanilla, citrus oils such as lemon oil, orange oil, grape and grapefruit oil, fruit essences including apple, peach, pear, strawberry, raspberry, cherry, plum, pineapple, and apricot.

(vii) Sweeten

Non-limiting examples of sweeteners include glucose (corn syrup), dextrose, invert sugar, fructose, and mixtures thereof (when not used as a carrier); saccharin and its various salts such as the sodium salt; dipeptide sweeteners such as aspartame; dihydrochalcone compounds, glycyrrhizin; *Stevie rebaudiana* (Stevioside); chloro derivatives of sucrose such as sucralose; sugar alcohols such as sorbitol, mannitol, sylitol, hydrogenated starch hydrolysates and the synthetic sweetener 3,6-dihydro-6-methyl-1,2,3-oxathiazin-4-one-2, 2-dioxide, particularly the potassium salt (acesulfame-K), and sodium and calcium salts thereof.

(viii) Dispersants

Dispersants may include but are not limited to starch, alginic acid, polyvinylpyrrolidones, guar gum, kaolin, bentonite, purified wood cellulose, sodium starch glycolate, isoamorphous silicate, and microcrystalline cellulose as high HLB emulsifier surfactants.

(ix) Coloring Agents

Suitable coloring agents include but are not limited to food, drug and cosmetic colors (FD&C), drug and cosmetic colors (D&C), or external drug and cosmetic colors (Ext. D&C). These colors or dyes, along with their corresponding lakes, and certain natural and derived colorants may be suitable for use in various embodiments.

(x) Taste-Masking Agents

Taste-masking agents include but are not limited to cellulose hydroxypropyl ethers (HPC) such as Klucel®, Nisswo HPC and PrimaFlo HP22; low substituted hydroxypropyl ethers (L-HPC); cellulose hydroxypropyl methyl ethers (HPMC) such as Seppifilm-LC, Pharmacoat®, Metolose SR; Opadry YS, PrimaFlo, MP3295A, Benecel MP824, and Benecel MP843; methylcellulose polymers such as Methocel® and Metolose®; Ethylcelluloses (EC) and mixtures thereof such as E461 Ethocel®, Aqualon®-EC, Surelease; Polyvinyl alcohol (PVA) such as Opadry AMB; hydroxyethylcelluloses such as Natrosol®; carboxymethylcelluloses and salts of carboxymethylcelluloses (CMC) such as Aualon®-CMC; polyvinyl alcohol and polyethylene glycol co-polymers such as Kollicoat IR®; monoglycerides (Myverol), triglycerides (KLX), polyethylene glycols, modified food starch, acrylic polymers and mixtures of acrylic polymers with cellulose ethers such as Eudragit® EPO, Eudragit® RD100, and Eudragit® E100; cellulose acetate phthalate; sepifilms such as mixtures of HPMC and stearic acid, cyclodextrins, and mixtures of these materials. In other embodiments, additional taste-masking agents contemplated are those described in U.S. Pat. Nos. 4,851,226, 5,075,114, and 5,876,759, each of which is hereby incorporated by reference in its entirety.

(xi) Release-Controlling Polymers

Release-controlling polymers may be included in the various embodiments of the solid dosage pharmaceutical compositions incorporating the granules. In one embodiment, the release-controlling polymers may be used as a tablet coating. In other embodiments, including but not limited to bilayer tablets, a release-controlling polymer may be mixed with the granules and other excipients prior to the formation of a tablet by a known process including but not limited to compression in a tablet mold. Suitable release-controlling polymers include but are not limited to hydrophilic polymers and hydrophobic polymers.

Suitable hydrophilic polymers include, but are not limited to, cellulose acetate, cellulose diacetate, cellulose triacetate, cellulose ethers, hydroxyethyl cellulose, hydroxypropyl cellulose, hydroxypropyl methylcellulose, microcrystalline cellulose, nitrocellulose, crosslinked starch, agar, casein, chitin, collagen, gelatin, maltose, mannitol, maltodextrin, pectin, pullulan, sorbitol, xylitol, polysaccharides, ammonia alginate, sodium alginate, calcium alginate, potassium alginate, propylene glycol alginate, alginate sodium carmellose, calcium carmellose, carrageenan, fucoidan, furcellaran, arabicgum, carrageensgum, ghaftigum, guargum, karayagum, locust beangum, okragum, tragacanthgum, scleroglucangum, xanthangum, hypnea, laminaran, acrylic polymers, acrylate polymers, carboxyvinyl polymers, copolymers of maleic anhydride and styrene, copolymers of maleic anhydride and ethylene, copolymers of maleic anhydride propylene or copolymers of maleic anhydride isobutylene), crosslinked polyvinyl alcohol and poly N-vinyl-2-pyrrolidone, diesters of polyglucan, polyacrylamides, polyacrylic acid, polyamides, polyethylene glycols, polyethylene oxides, poly(hydroxyalkyl methacrylate), polyvinyl acetate, polyvinyl alcohol, polyvinyl chloride, polystyrenes, polyvinylpyrrolidone, anionic and cationic hydrogels, and combinations thereof.

Non-limiting examples of suitable hydrophobic polymers include cellulose acetate butyrate, cellulose acetate ethylcarbamate, cellulose acetate heptanoate, cellulose acetate methylcarbamate, cellulose acetate octanoate, cellulose acetate phthalate, cellulose acetate propionate, cellulose acetate succinate, cellulose acetate trimaletate, cellulose acetaldehyde dimethyl acetate, cellulose butyrate, cellulose dimethylaminoacetate, cellulose disuccinate, cellulose dipalmitate, cellulose dicaprylate, cellulose propionate, cellulose propionate succinate, cellulose trioctanoate, cellulose tripropionate, cellulose trimellitate, cellulose tripalmitate, cellulose trivalerate, cellulose valerate palmitate, carboxymethyl cellulose, calcium carboxymethyl cellulose, sodium carboxymethyl cellulose, ethyl cellulose, ethylhydroxy ethylcellulose, hydroxy propyl methylcellulose phthalate, methyl cellulose, methyl ethyl cellulose, propyl cellulose, sodium carboxymethyl starch, polyvinyl acetate phthalate, polyvinyl alcohol phthalate, methacrylic acid copolymers, methacrylic acid ester copolymers, methyl methacrylate copolymers, ethoxyethyl methacrylates, cyanoethyl methacrylate, aminoalkyl methacrylate copolymer, poly(acrylate), poly(methacrylate), poly (methyl methacrylate), poly(ethylacrylate), poly(ethyl methacrylate), poly(methacrylic acid anhydride), glycidyl methacrylate copolymers, ammonia methacrylate copolymers, lecithins, aluminum monostearate, cetylalcohol, hydrogenated beef tallow, hydrogenated castor oil, hydrogenated vegetable oil, 12-hydroxystearyl alcohol, glyceryl monopalmitate, glyceryl dipalmitate, glyceryl monostearate, glyceryl distearate, glyceryl tristearate, myristyl alcohol, stearic acid, stearyl alcohol, polyethyleneglycols, zein, shellac, bee's wax, carnauba wax, glyceryl behenate, Japan wax, paraffin, spermaceti, synthetic waxes, and combinations thereof.

(b) Methods of Producing Solid Dosage Forms

The solid dosage pharmaceutical compositions may be produced using any suitable method known in the art. The particular production method selected may depend on the desired type of solid dosage form and the desired release profile.

(i) Production of Tablet Compositions

The pharmaceutical compositions in the form of a tablet may be produced using any suitable method known in the art including but not limited to direct compression, wet granulation, dry granulation, and combinations thereof. In one embodiment, the morphinan-protected granules may be combined with the one or more carriers and granulated into tablet granules using any of the known granulation devices described previously. In this same embodiment, the tablet granules formed from the combination of the morphinan-protected granules and the one or more carriers may be optionally blended with one or more additional carriers including but not limited to lubricants, and the resulting tablet blend may be compressed into a tablet form. In another embodiment, one or more carriers incorporated into the tablet granules may include a release-controlling polymer to impart a modified release profile to the resulting tablet.

In yet another embodiment, a bilayer tablet may be formed by producing a first tablet blend and a second tablet blend using a tablet granulation and blending process similar to those previously described. In this embodiment, the first tablet blend may include a disintegrant in order to impart a rapid release profile to the resulting tablet produced using the first tablet blend. The second tablet blend of this embodiment may include a release-controlling polymer to impart a modified release profile to the resulting tablet produced using the second tablet blend. The first tablet blend and the second tablet blend may be loaded into a tableting device including but not limited to a bilayer tablet press, and pressed into a bilayer tablet in which the first layer may have a rapid release profile and the second layer may have a modified release profile.

In yet another embodiment, the morphinan-protected granules may be coated with a release-controlling polymer prior to incorporating the morphinan-protected granules into a solid tablet form in order to impart a modified release profile to the resulting tablet. In an additional embodiment, the solid tablet form may be coated with a release-controlling polymer to impart a modified release profile. Other combinations of the embodiments described above may be used to produce additional embodiments having a desired release profile or other desired performance characteristic including but not limited to masked taste, acceptable tongue-feel and mouth-feel, and enhanced stability.

(ii) Production of Capsule Compositions

The pharmaceutical compositions in the form of a capsule may be produced using any suitable method known in the art including but not limited to direct loading into two-piece telescoping hard capsules. Non-limiting examples of suitable hard capsules include hard starch capsules, hard gelatin capsules, and hard cellulose capsules. In one embodiment, the capsule form of the pharmaceutical compositions may be produced by loading the morphinan-protected granules in to the hard capsule and sealing the capsule. In other embodiments, the morphinan-protected granules may be coated with a release-controlling polymer to impart a modified release profile to the hard capsule composition. In yet other embodiments, a fraction of the morphinan-protected granules may be coated with a release-controlling polymer and combined with the remaining uncoated morphinan-protected granules prior to loading the granules into the hard capsule.

(VI) Exemplary Embodiments

Exemplary embodiments of a granule and a solid dose pharmaceutical composition are described below.

(a) Oxycodone-Protected Granule

An exemplary embodiment of a granule includes oxycodone, microcrystalline cellulose, pregelatinized starch, $Na_2EDTA$, and citric acid. The overall composition of the exemplary oxycodone-protected granule embodiment is listed in Table 10 below. In this embodiment, the granules may be formed using the wet granulation method described in Example 5 below. In this embodiment, the oxycodone granules have a granule $d_{90}$ ranging from about 100 µm to about 400 µm, and contain less than about 2% water by weight.

(b) Bilayer Oxycodone/APAP Tablet

An exemplary embodiment of a solid dose pharmaceutical composition may be a bilayer tablet that includes the oxycodone-protected granules described above. The exemplary bilayer tablet may be formed using the method described in Example 2 below. The two layers of the bilayer tablet in this embodiment include an immediate release (IR) layer and a sustained release (SR) layer. The overall compositions of the IR layer and the sustained release layer of the exemplary bilayer tablet embodiment are listed in Table 1 below. The stability of the oxycodone in the exemplary bilayer tablet composition that incorporates oxycodone in a granular form is significantly better than a similar bilayer tablet composition that incorporates oxycodone in an unprotected powder form, as described in Example 2 below.

TABLE 1

Composition of Exemplary Oxycodone Bilayer Tablet Composition

| Compound | Dry Wt. (% total) | |
|---|---|---|
|  | IR Layer | SR Layer |
| Protected oxycodone granules | 2.99% | 2.62% |
| APAP | 77.73% | 22.73% |
| MCC | 4.82% | 26.81% |
| Hydroxypropyl cellulose | 7.71% | 1.34% |
| Cross carmellose sodium | 6.00% |  |
| Silicon dioxide | 0.50% | 0.5% |
| Magnesium stearate | 0.25% | 1.0% |
| Polyethylene oxide polymer |  | 45.0% |

(c) Hydrocodone-Protected Granule

An exemplary embodiment of a granule includes hydrocodone, microcrystalline cellulose, pregelatinized starch. $Na_2EDTA$, and citric acid. The overall composition of the exemplary hydrocodone-protected granule embodiment is listed in Table 13 below. In this embodiment, the granules may be formed using the wet granulation method described in Example 6 below. In this embodiment, the hydrocodone granules have a granule $d_{90}$ ranging from about 100 µm to about 400 µm after milling, and contain less than about 5% water by weight.

(d) Bilayer Hydrocodone/APAP Tablet

An exemplary embodiment of a solid dose pharmaceutical composition may be a bilayer tablet that includes the hydrocodone-protected granules described above. The exemplary bilayer tablet may be formed using the method described in Example 2 below. The two layers of the bilayer tablet in this embodiment include an immediate release (IR) layer and a sustained release (SR) layer. The overall compositions of the IR layer and the sustained release layer of the exemplary bilayer tablet embodiment are listed in Table 2 below. The stability of the hydrocodone in the exemplary bilayer tablet composition that incorporates hydrocodone in a granular form is significantly better than a similar bilayer tablet composition that incorporates hydrocodone in an unprotected powder form.

TABLE 2

Composition of Exemplary Hydrocodone Bilayer Tablet Composition

| Compound | Dry Wt (% total) | |
|---|---|---|
| | IR Layer | SR Layer |
| Protected hydrocodone granules | 2.99% | 2.62% |
| APAP | 77.73% | 22.73% |
| MCC | 4.82% | 26.81% |
| Hydroxypropyl cellulose | 7.71% | 1.34% |
| Cross carmellose sodium | 8.00% | |
| Silicon dioxide | 0.50% | 0.5% |
| Magnesium stearate | 0.25% | 1.0% |
| Polyethylene oxide polymer | | 45.0% |

EXAMPLES

The following examples demonstrate various aspects of the invention.

Example 1

Incorporation of Protected Oxycodone Granules into Bilayer Tablet Composition

To demonstrate the feasibility of forming protected morphinan granules and incorporating the protected morphinan granules into a solid dosage form, the following experiment was conducted.

Powdered oxycodone HCl, microcrystalline cellulose (MCC), and citric acid powder (an antioxidant) were mixed together and charged into a high-shear granulator. An aqueous solution containing pregelatinized starch (PGS) and Na$_2$EDTA (an antioxidant) was sprayed into the high-speed granulator, resulting in the formation of wet granules. The wet granules were then dried until less than about 2% water remained in the granules. The dried granules had particle sizes ranging from about 100-300 µm. The composition of the protected oxycodone granules is summarized in Table 3:

TABLE 3

Composition of Protected Oxycodone Granules

| Compound | Dry Weight (% tot. wt.) |
|---|---|
| Oxycodone HCl | 30.0% |
| MCC | 63.6% |
| PGS | 4.0% |
| Na$_2$EDTA | 0.4% |
| Citric acid | 2.0% |

The oxycodone-protected granules were divided into two groups to be incorporated into batches of immediate release (IR) granules and into batches of sustained release (SR) granules used to form the IR and SR Layers of a bilayer tablet, respectively. Both the IR granules and the SR granules were formed using separate fluid bed granulation processes. In each process, the previously-formed protected oxycodone granules, powdered acetaminophen (APAP), and various excipients including disintegrants, binders; and fillers were charged into the fluid bed granulation device and sprayed with a granulation fluid, resulting in the formation of IR granules in one batch and SR granules in a second batch. The composition of the resulting IR and SR granules are summarized in Table 4:

TABLE 4

Composition of IR and SR Granules

| Compound | Dry Wt (% total wt.) | |
|---|---|---|
| | IR Layer | SR Layer |
| Protected oxycodone granules | 16.1% | 14.2% |
| APAP | 67.8% | 81.2% |
| MCC | 5.0% | |
| Hydroxypropyl cellulose | 8.1% | 4.5% |
| Cross carmellose sodium | 3.0% | |

The IR granules were blended with lubricant excipients in preparation for the tablet pressing process. Similarly, the SR particles were blended with various excipients including lubricants, and polyethylene oxide polymer, and a filler in preparation for the tablet pressing process. The compositions of the IR blend and the SR blend are summarized in Table 5:

TABLE 5

Composition of IR and SR Blends

| Compound | Dry Wt. (% total wt.) | |
|---|---|---|
| | IR Blend | SR Blend |
| IR granules | 99.25% | |
| SR granules | | 52.30% |
| Silicon dioxide | 0.50% | 0.50% |
| Magnesium stearate | 0.25% | 0.10% |
| MCC | | 1.20% |
| Polyethylene oxide polymer | | 45.00% |

The IR blend and the SR blend were loaded into a bilayer tablet press and formed into bilayer tablets having about 29% of the IR blend and about 71% the SR blend by weight.

The results of this experiment demonstrated that protected morphinan granules could be formed using a process of high shear wet granulation and incorporated into a solid oral therapeutic composition.

Example 2

Oxidative Stability Assessment of Bilayer Tablet Composition

To assess the effect of incorporating a morphinan in the form of protected granules into a solid dosage therapeutic composition on the oxidative stability of the composition, the following experiment was conducted.

Unprotected bilayer tablets were formed using a process similar to that described in Example 1, except that powdered oxycodone HCl, rather than protected oxycodone granules, were incorporated into the IR and SR granules formed using the fluid bed granulation device. Protected bilayer tablets formed using protected oxycodone granules as described in Example 1 were also obtained. The unprotected bilayer tablets were similar in composition to the protected bilayer tablets, except that the unprotected bilayer tablets lacked antioxidant excipients and oxycodone-protected granules, although the overall oxycodone contents of the two formulations of bilayer tablet were comparable.

A batch of protected bilayer tablets and a batch of unprotected tablets were placed into an environmental chamber and exposed to accelerated stability conditions. In particular, all bilayer tablets were kept in the environmental chamber at a temperature of 55° C. and a relative humidity of 80% for a period of six days. For the remainder of the first month and for the duration of a second month, the bilayer tablets were exposed to a temperature of 4° C. and a relative humidity of 75%.

After six days, one month, and two months in the environmental chamber, samples of the protected and unprotected formulations were removed from the chamber and submitted to mass spectrographic analysis to determine the presence of three oxidative degradants of oxycodone: dihydroxy oxycodone, oxycodone n-oxide, and 10-hydroxy oxycodone. The results of these analyses are summarized in Table 6 below:

TABLE 6

Oxidative Stability of Unprotected vs. Protected Formulations of Bilayer Tablets

| Degradation Conditions | | | Amount of Degradant Formed (% weight of oxycodone) | | | | | |
|---|---|---|---|---|---|---|---|---|
| | | | Di-hydroxy oxycodone | | 10-hydroxy oxycodone | | Oxycodone n-oxide | |
| Time (days) | Temp. (° C.) | Relative Humidity (%) | Not Protected | Protected | Not Protected | Protected | Not Protected | Protected |
| 6 | 55 | 80 | 0.20 | 0.00 | 0.04 | 0.00 | 0.12 | 0.03 |
| 30 | 40 | 75 | 0.05 | 0.01 | 0.01 | 0.00 | 0.12 | 0.01 |
| 60 | 40 | 75 | 0.11 | 0.02 | 0.03 | 0.00 | 0.21 | 0.03 |

The protected formulation of the bilayer tablets that incorporated the oxycodone-protected granules had significantly lower levels of all degradants after exposure to all environmental conditions. No 10-hydroxy oxycodone was measured at any environmental condition for the protected formulation of the bilayer tablet.

The results of this experiment demonstrated that the formation of oxidative degradants of oxycodone was significantly inhibited by the incorporation of the oxycodone in the form of protected granules. In particular, the bilayer tablets formed using the protected oxycodone granules were significantly more stable than similar bilayer tablets formed using unprotected oxycodone powder.

Example 3

Effect of Granule Composition on Oxidative Stability

To assess the effect of various granule compositions on the oxidative stability of the morphinan encapsulated in the granules, the following experiment was conducted.

Granules containing oxycodone and various combinations of excipients were formed using methods similar to those described in Example 1. The specific compositions of the granules are summarized in Table 7:

TABLE 7

Composition of IR and SR Granules

| Compound | Granule Composition (% w/w) | | | | |
|---|---|---|---|---|---|
| | 1 | 2 | 3 | 5 | 6 |
| Oxycodone | 30 | 30 | 30 | 30 | 30 |
| MCC | 65 | 64.95 | 62.2 | 64.95 | 62.2 |
| HPC | 5 | 4.6 | 4.6 | | |
| BHA | | 0.05 | | 0.05 | |
| EDTA | | 0.4 | 0.4 | 0.4 | 0.4 |
| Ascorbic Acid | | | 2.8 | | 2.8 |
| PGS | | | | 4.6 | 4.6 |

For granule compositions 1, 2, and 3 the HPC and EDTA were dissolved in a granulation solution and applied to a dry mixture of the remaining ingredients. For granule compositions 5 and 6, the PGS and EDTA were dissolved in a granulations solution and applied to a dry mixture of the remaining ingredients.

The resulting granules were stored at accelerated stability conditions for a period of 4 weeks at 40° C. and 75% relative humidity. Samples of the granules were taken just before storage and after one, two, and four weeks of storage at accelerated stability conditions and subjected to mass spectrographic analysis as described in Example 2 to determine the presence of oxidative degradants of oxycodone. The results of the analyses of the samples taken after four weeks of storage are summarized in Table 8 below:

TABLE 8

Oxidative Stability of Granule Formulations

| | Impurity After 4 Weeks at Accelerated Degradation Conditions (% wt of oxycodone) | |
|---|---|---|
| Composition | 6-a-Oxycodol | Noroxy |
| 1 | 0.11 | 0.01 |
| 2 | 0.11 | 0.02 |
| 3 | 0.33 | 0.13 |
| 5 | 0.11 | 0.00 |
| 6 | 0.29 | 0.14 |

The impurities for granule compositions 1, 2, and 5 were all of comparable low amounts, indicating that the granulation of the oxycodone resulted in a protective effect from oxidative degradation. This protective effect was achieved even in granule composition 1, which did not include any antioxidant excipients. However, granule compositions 3 and 6, which contained ascorbic acid, resulted in much higher levels of oxidative impurities after 4 weeks of storage at accelerated stability conditions, indicating that the ascorbic acid may produce oxidative products that result in the long-term degradation of the oxycodone.

The results of this experiment demonstrated the protective effect of granulation against the oxidative degradation of oxycodone, so long as ascorbic acid was not included in the granule composition.

Example 4

Effect of Granulation Composition on Oxidative Stability of Solid Dose Oxycodone/APAP Formulations To assess the effect of encapsulation on the oxidative stability of the morphinan in various solid dose formulations, the following experiment was conducted.

Solid dose tablets were formed using the methods described in Example 2. The solid dose tablets contained the oxycodone either in the protected granular form described in Example 3, or as the same ingredients in a powdered form rather than as granules. In both cases, the oxycodone and excipients were combined with APAP and polyethylene oxide (PEO) polymer. Each tablet contained 10% of the oxycodone granule compositions described in Example 3, in either granulated or powdered form, 46.8% APAP, and 43.2% PEO polymer on a weight basis.

The protected and unprotected tablet formulations were stored at accelerated stability conditions for a period of 4 weeks at 40° C. and 75% relative humidity. Samples of the tablets were taken just before storage and after one, two, and four weeks of storage at accelerated stability conditions and subjected to mass spectrographic analysis as described in Example 2 to determine the presence of oxidative degradants of oxycodone. The results of these analysis of the samples taken after four weeks of storage are summarized in Table 9 below:

TABLE 9

Effect of Granulation on Oxidative Stability of Tablet Formulations

| Composition Combined with APAP and PEO Polymer | Impurity After 4 Weeks at Accelerated Degradation Conditions (% wt of oxycodone) | | | |
|---|---|---|---|---|
| | 6-a-Oxycodol | | Noroxy | |
| | Protected granules | Unprotected | Protected Granules | Unprotected |
| 1 | 0.20 | .74 | 0.03 | .27 |
| 2 | 0.22 | .51 | 0.05 | .28 |
| 3 | 0.60 | 1.25* | 0.11 | .14* |
| 5 | 0.17 | .49 | 0.01 | .18 |

*measured at two weeks after storage

All of the protected tablet formulations, in which the oxycodone was granulated using methods similar to those described in Example 1 formed significantly lower levels of impurities after storage for 4 weeks at accelerated stability conditions compared to tablets containing non-granulated oxycodone and the same excipients The results of this experiment demonstrated that granulating the oxycodone and excipients prior to incorporating the granules in a tableting process resulted in tablets with superior stability compared to tablets formed using the same oxycodone and excipients in a loose powder form, independent of the particular composition of excipients in the formulation.

Example 5

Incorporation of Protected Oxycodone Granules into Bilayer Tablet Composition

To demonstrate the feasibility of forming protected morphinan granules and incorporating the protected morphinan granules into a solid dosage form, the following experiment was conducted to prepare a 7.5 mg oxycodone/325 mg acetaminophen tablet.

Powdered oxycodone HCl, microcrystalline cellulose (MCC), pregelatinized starch (PGS), $Na_2EDTA$ (an antioxidant), and citric acid powder (an antioxidant) were charged into a high-shear granulator and mixed together. An aqueous solution containing pregelatinized starch (PGS) was sprayed into the high-speed granulator, resulting in the formation of wet granules. The wet granules were then dried until less than about 5% water remained in the granules. The dried granules had particle sizes ranging from about 100-300 μm after milling. The composition of the oxycodone-protected granules is summarized in Table 10:

TABLE 10

Composition of Protected Oxycodone Granules

| Compound | Dry Weight (% tot. wt.) |
|---|---|
| Oxycodone HCl | 30.0% |
| MCC | 63.6% |
| PGS | 4.0% |
| $Na_2EDTA$ | 0.4% |
| Citric acid | 2.0% |

The oxycodone-protected granules were divided into two groups to be incorporated into batches of immediate release (IR) granules and into batches of sustained release (SR) granules used to form the IR and SR Layers of a bilayer tablet, respectively. Both the IR granules and the SR granules were formed using separate fluid bed granulation processes. In each process, the previously-formed oxycodone-protected granules, powdered acetaminophen (APAP), and various excipients including disintegrants, binders, and fillers were charged into the fluid bed granulation device and sprayed with a granulation fluid, resulting in the formation of IR granules in one batch and SR granules in a second batch. The composition of the resulting IR and SR granules are summarized in Table 11:

TABLE 11

Composition of IR and SR Granules

| | Dry Wt. (% total wt.) | |
|---|---|---|
| Compound | IR Granules | SR Granules |
| Protected oxycodone granules | 3.10% | 9.79% |
| APAP | 80.65% | 84.81% |
| MCC | 5.0% | |
| Hydroxypropyl cellulose | 8.0% | 5.0% |
| Cross carmellose sodium | 3.0% | |
| Silicon Dioxide | 0.25% | 0.4% |

The IR granules were blended with lubricant excipients in preparation for the tablet pressing process. Similarly, the SR particles were blended with various excipients including lubricants, and polyethylene oxide polymer, and a filler in preparation for the tablet pressing process. The compositions of the IR blend and the SR blend are summarized in Table 12:

TABLE 12

Composition of IR and SR Blends

| Compound | Dry Wt. (% total wt.) | |
|---|---|---|
| | IR Blend | SR Blend |
| IR granules | 96.38% | |
| SR granules | | 26.80% |
| Croscarmellose Sodium | 3.11% | |
| Silicon dioxide | 0.26% | 0.39% |
| Magnesium stearate | 0.25% | 1.0% |
| MCC | | 26.81% |
| Polyethylene oxide polymer | | 45.00% |

The IR blend and the SR blend were loaded into a bilayer tablet press and formed into bilayer tablets having about 23% of the IR blend and about 77% the SR blend by weight.

The results of this experiment demonstrated that protected morphinan granules could be formed using a process of high shear wet granulation and incorporated into a solid oral therapeutic composition.

Example 6

Incorporation of Protected Hydrocodone Granules into Bilayer Tablet Composition

To demonstrate the feasibility of forming protected morphinan granules and incorporating the protected morphinan granules into a solid dosage form, the following experiment was conducted to prepare a 7.5 mg hydrocodone/325 mg acetaminophen tablet.

Powdered hydrocodone bitartrate, microcrystalline cellulose (MCC), pregelatinized starch (PGS) and citric acid powder (an antioxidant) were mixed together and charged into a high-shear granulator. An aqueous solution containing pregelatinized starch (PGS) and Na$_2$EDTA (an antioxidant) was sprayed into the high-speed granulator, resulting in the formation of wet granules. The wet granules were then dried until less than about 5% water remained in the granules. The dried granules had particle sizes ranging from about 100-300 μm after milling. The composition of the protected hydrocodone granules is summarized in Table 13:

TABLE 13

Composition of Protected Hydrocodone Granules

| Compound | Dry Weight (% tot. wt.) |
|---|---|
| Hydrocodone bitartrate | 30.0% |
| MCC | 63.6% |
| PGS | 4.0% |
| Na$_2$EDTA | 0.4% |
| Citric acid | 2.0% |

The hydrocodone-protected granules were divided into two groups to be incorporated into batches of immediate release (IR) granules and into batches of sustained release (SR) granules used to form the IR and SR Layers of a bilayer tablet, respectively. Both the IR granules and the SR granules were formed using separate fluid bed granulation processes. In each process, the previously-formed protected hydrocodone granules, powdered acetaminophen (APAP), and various excipients including disintegrants, binders, and fillers were charged into the fluid bed granulation device and sprayed with a granulation fluid, resulting in the formation of IR granules in one batch and SR granules in a second batch. The composition of the resulting IR and SR granules are summarized in Table 14:

TABLE 14

Composition of IR and SR Granules

| Compound | Dry Wt. (% total wt.) | |
|---|---|---|
| | IR Granules | SR Granules |
| Protected hydrocodone granules | 3.10% | 9.79% |
| APAP | 80.65% | 84.81% |
| MCC | 5.0% | |
| Hydroxypropyl cellulose | 8.0% | 5.0% |
| Cross carmellose sodium | 3.0% | |
| Silicon Dioxide | 0.25% | 0.4% |

The IR granules were blended with lubricant excipients in preparation for the tablet pressing process. Similarly, the SR particles were blended with various excipients including lubricants, and polyethylene oxide polymer, and a filler in preparation for the tablet pressing process. The compositions of the IR blend and the SR blend are summarized in Table 15:

TABLE 15

Composition of IR and SR Blends

| Compound | Dry Wt. (% total wt.) | |
|---|---|---|
| | IR Blend | SR Blend |
| IR granules | 96.38% | |
| SR granules | | 26.80% |
| Croscarmellose Sodium | 3.11% | |
| Silicon dioxide | 0.26% | 0.39% |
| Magnesium stearate | 0.25% | 1.0% |
| MCC | | 28.81% |
| Polyethylene oxide polymer | | 45.00% |

The IR blend and the SR blend were loaded into a bilayer tablet press and formed into bilayer tablets having about 23% of the IR blend and about 77% the SR blend by weight.

The results of this experiment demonstrated that protected morphinan granules could be formed using a process of high shear wet granulation and incorporated into a solid oral therapeutic composition.

Having described the invention in detail, it will be apparent that modifications and variations are possible. Those of skill in the art should, in light of the present disclosure, appreciate that many changes could be made in the specific embodiments that are disclosed and still obtain a like or similar result without departing from the spirit and scope of the invention, therefore all matter set forth is to be interpreted as illustrative and not in a limiting sense.

What is claimed is:

1. A granule substantially resistant to oxidative degradation of hydrocodone, the granule comprising an interior region substantially comprising the hydrocodone and an exterior region substantially comprising at least one excipient chosen from a binder, a filler, an antioxidant, a chelating agent, and combinations thereof, wherein the exterior region surrounds the interior region and wherein the granule contains less than about 0.5 w/w of the total mass of hydrocodone of one or more of a degradant selected from hydrocodone-n-oxide and hydrocodone aldol dimer after being stored for 6 months at 40° C. and 75% relative humidity.

2. The granule of claim 1, wherein less than about 20% of the total weight of the hydrocodone in the granule is exposed on the surface of the granule.

3. The granule of claim 1, further comprising at least one additional active pharmaceutical ingredient.

4. The granule of claim 2, wherein the at least one additional active pharmaceutical ingredient is acetaminophen.

5. A solid dosage pharmaceutical composition comprising a plurality of hydrocodone protected granules and acetaminophen, the composition prepared by a process comprising:
 (a) granulating a first mixture comprising the hydrocodone and at least one excipient to form the plurality of hydrocodone protected granules, wherein the hydrocodone in the hydrocodone protected granules is substantially resistant to oxidative degradation and wherein the granule contains less than about 0.5% w/w of the total mass of hydrocodone of one or more of a degradant selected from hydrocodone-n-oxide and hydrocodone aldol dimer after being stored for 6 months at 40° C. and 75% relative humidity;
 (b) granulating a second mixture in the presence of a granulation fluid, the second mixture comprising the plurality of hydrocodone protected granules, the acetaminophen, and at least one additional excipient to form a plurality of tablet granules; and
 (c) blending the plurality of tablet granules with a release-controlling polymer and optionally at least one pharmaceutically acceptable carrier to form the solid dosage pharmaceutical composition comprising a sustained release layer.

6. The solid dosage pharmaceutical composition of claim 5, further comprising step (d) which includes granulating a third mixture in the presence of a granulation fluid, the third mixture comprising hydrocodone protected granules, acetaminophen, and at least one additional excipient to form a plurality of immediate release granules, and step (e) blending the immediate release granules with at least one excipient to form an immediate release layer.

7. The solid dosage pharmaceutical composition of claim 5, wherein less than about 30% of the total weight of the hydrocodone in the protected granules is exposed on the surface of the granules.

8. The solid dosage pharmaceutical composition of claim 5, wherein the at least one pharmaceutically acceptable carrier is incompatible with the hydrocodone.

9. The solid dosage pharmaceutical composition of claim 5, wherein the release-controlling polymer is a hydrophilic polymer.

10. The solid dosage pharmaceutical composition of claim 9, wherein the hydrophilic polymer is a polyethylene oxide.

* * * * *